(12) United States Patent
Matsuyama

(10) Patent No.: US 9,976,148 B2
(45) Date of Patent: May 22, 2018

(54) YEAST TERMINATOR AND USE THEREFOR

(71) Applicant: KABUSHIKI KAISHA TOYOTA CHUO KENKYUSHO, Nagakute-shi, Aichi-ken (JP)

(72) Inventor: Takashi Matsuyama, Nagakute (JP)

(73) Assignee: KABUSHIKI KAISHA TOYOTA CHUO KENKYUSHO, Nagakute-shi (JP)

( * ) Notice: Subject to any disclaimer, the term of this patent is extended or adjusted under 35 U.S.C. 154(b) by 0 days. days.

(21) Appl. No.: 15/393,788

(22) Filed: Dec. 29, 2016

(65) Prior Publication Data

US 2017/0198296 A1 Jul. 13, 2017

(30) Foreign Application Priority Data

Jan. 8, 2016 (JP) .................................. 2016-003052

(51) Int. Cl.
| | | |
|---|---|---|
| *C12P 21/00* | (2006.01) | |
| *C12N 15/67* | (2006.01) | |
| *C12N 15/81* | (2006.01) | |
| *C07H 21/04* | (2006.01) | |

(52) U.S. Cl.
CPC ............. *C12N 15/67* (2013.01); *C12N 15/81* (2013.01); *C12P 21/00* (2013.01)

(58) Field of Classification Search
None
See application file for complete search history.

(56) References Cited

U.S. PATENT DOCUMENTS

| | | |
|---|---|---|
| 9,371,534 B2 | 6/2016 | Matsuyama et al. |
| 9,512,436 B2 | 12/2016 | Matsuyama et al. |
| 2013/0244243 A1 | 9/2013 | Matsuyama et al. |
| 2016/0281097 A1 | 9/2016 | Matsuyama et al. |

FOREIGN PATENT DOCUMENTS

| | | |
|---|---|---|
| JP | 2014-039533 A | 3/2014 |
| JP | 2015-136303 A | 7/2015 |

OTHER PUBLICATIONS

Yamanishi M et al. "A Genome-Wide Activity Assessment of Terminator Regions in *Saccharomyces cerevisiae* Provides a "Terminatome" Toolbox." ACS Synth Biol, 2, Feb. 11, 2013.
Ito Y et al. "Characterization of Five Terminator Regions That Increase the Protein Yield of a Transgene in *Saccharomyces cerevisiae*." J Biotechnol, 168, 2013.

*Primary Examiner* — Nancy J Leith
(74) *Attorney, Agent, or Firm* — Oliff PLC

(57) ABSTRACT

A yeast terminator derived from a yeast DIT1 terminator when aligned with the nucleotide sequence represented by SEQ ID NO:1, includes a partial nucleotide sequence corresponding to the partial nucleotide sequence AGTTCG of positions 54 to 59 in the nucleotide sequence represented by SEQ ID NO:1, and also includes one or two or more mutations selected from the group made of (a) to (c): (a) a first mutation substituting TTTTTCT for the partial nucleotide sequence TTTTGTTCT of positions 27 to 35 in the nucleotide sequence represented by SEQ ID NO:1; (b) a second mutation substituting TCTTT for the partial nucleotide sequence TCTCATTTT of positions 69 to 77 in the nucleotide sequence represented by SEQ ID NO:1; and (c) a third mutation substituting A for the G of position 51 in the nucleotide sequence represented by SEQ ID NO:1.

14 Claims, 7 Drawing Sheets

SEQUENCE LISTING

<160> NUMBER OF SEQ ID NOS: 54

<210> SEQ ID NO 1

```
<211> LENGTH: 247
<212> TYPE: DNA
<213> ORGANISM: Saccharomyces cerevisiae

<400> SEQUENCE: 1
agtaagagcg ctacattggt ctaccttttt gttcttttac ttaaacatta gttagttcgt    60 tttcttttc tcatttttt atgtttcccc cccaaagttc tgattttata atatttatt     120 tcacacaatt ccatttaaca gaggggaat agattcttta gcttagaaaa ttagtgatca    180
atatatattt gcctttcttt tcatcttttc agtgatatta atggtttcga gacactgcaa    240
tggccct                                                              247

<210> SEQ ID NO 2
<211> LENGTH: 244
<212> TYPE: DNA
<213> ORGANISM: Artificial Sequence
<220> FEATURE:
<223> OTHER INFORMATION: Mutant terminator

<400> SEQUENCE: 2
agtaagagcg ctacattggt ctaccttttt cttttactta aacattagtt agttcgtttt    60 cttttctca tttttttatg tttccccccc aaagttctga ttttataata ttttatttca    120
cacaattcca tttaacagag ggggaataga ttctttagct tagaaaatta gtgatcaata    180
tatatttgcc tttcttttca tcttttcagt gatattaatg gtttcgagac actgcaatgg    240
ccct                                                                  244

<210> SEQ ID NO 3
<211> LENGTH: 244
<212> TYPE: DNA
<213> ORGANISM: Artificial Sequence
<220> FEATURE:
<223> OTHER INFORMATION: Mutant terminator

<400> SEQUENCE: 3
agtaagagcg ctacattggt ctaccttttt gttcttttac ttaaacatta gttagttcgt    60 tttcttttc tttttttatg tttccccccc aaagttctga ttttataata ttttatttca    120
cacaattcca tttaacagag ggggaataga ttctttagct tagaaaatta gtgatcaata    180
tatatttgcc tttcttttca tcttttcagt gatattaatg gtttcgagac actgcaatgg    240
ccct                                                                  244

<210> SEQ ID NO 4
<211> LENGTH: 247
<212> TYPE: DNA
<213> ORGANISM: Artificial Sequence
<220> FEATURE:
<223> OTHER INFORMATION: Mutant terminator

<400> SEQUENCE: 4
agtaagagcg ctacattggt ctaccttttt gttcttttac ttaaacatta attagttcgt    60 tttcttttc tcatttttt atgtttcccc cccaaagttc tgattttata atatttatt     120 tcacacaatt ccatttaaca gaggggaat agattcttta gcttagaaaa ttagtgatca    180
atatatattt gcctttcttt tcatcttttc agtgatatta atggtttcga gacactgcaa    240
tggccct                                                              247

<210> SEQ ID NO 5
<211> LENGTH: 241
```

<212> TYPE: DNA
<213> ORGANISM: Artificial Sequence
<220> FEATURE:
<223> OTHER INFORMATION: Mutant terminator

<400> SEQUENCE: 5

```
agtaagagcg ctacattggt ctacctttt  cttttactta aacattagtt agttcgtttt      60
cttttctttt ttttatgttt ccccccaaa  gttctgattt tataatattt tatttcacac     120
aattccattt aacagagggg gaatagattc tttagcttag aaaattagtg atcaatatat     180
atttgccttt cttttcatct tttcagtgat attaatggtt tcgagacact gcaatggccc     240
t                                                                    241
```

<210> SEQ ID NO 6
<211> LENGTH: 241
<212> TYPE: DNA
<213> ORGANISM: Artificial Sequence
<220> FEATURE:
<223> OTHER INFORMATION: Mutant terminator

<400> SEQUENCE: 6

```
agtaagagcg ctacattggt ctacctttt  cttttactta aacattaatt agttcgtttt      60
cttttctttt ttttatgttt ccccccaaa  gttctgattt tataatattt tatttcacac     120
aattccattt aacagagggg gaatagattc tttagcttag aaaattagtg atcaatatat     180
atttgccttt cttttcatct tttcagtgat attaatggtt tcgagacact gcaatggccc     240
t                                                                    241
```

<210> SEQ ID NO 7
<211> LENGTH: 237
<212> TYPE: DNA
<213> ORGANISM: Artificial Sequence
<220> FEATURE:
<223> OTHER INFORMATION: Mutant terminator

<400> SEQUENCE: 7

```
agtaagagcg ctacattggt ctacctttt  gttctttac ttaaacacgt tttcttttc       60
tcattttttt atgtttcccc cccaaagttc tgatttata atattttatt tcacacaatt     120
ccatttaaca gaggggaat agattcttta gcttagaaaa ttagtgatca atatatattt     180
gcctttcttt tcatctttc agtgatatta atggtttcga gacactgcaa tggccct       237
```

<210> SEQ ID NO 8
<211> LENGTH: 244
<212> TYPE: DNA
<213> ORGANISM: Artificial Sequence
<220> FEATURE:
<223> OTHER INFORMATION: Mutant terminator

<400> SEQUENCE: 8

```
agtaagagcg ctacattggt ctacctttt  cttttactta aacattagtt agttcgtttt      60
cttttctca tttttttatg tttccccccc aaagttctga ttttataata ttttatttca     120
cacaattcca tttaacagag ggggaataga ttctttagct tagaaaatta gtgatcaata     180
tatatttgcc tttcttttca tctttcagt gatattaatg gtttcgagac actgcaatgg     240
ccct                                                                244
```

<210> SEQ ID NO 9
<211> LENGTH: 244
<212> TYPE: DNA

<213> ORGANISM: Artificial Sequence
<220> FEATURE:
<223> OTHER INFORMATION: Mutant terminator

<400> SEQUENCE: 9

```
agtaagagcg ctacattggt ctacctttt gttttactta aacattagtt agttcgtttt    60
cttttctca ttttttatg tttcccccc aaagtctga ttttataata ttttatttca      120
cacaattcca tttaacagag ggggaataga ttctttagct tagaaaatta gtgatcaata   180
tatatttgcc tttcttttca tcttttcagt gatattaatg gtttcgagac actgcaatgg   240
ccct                                                                244
```

<210> SEQ ID NO 10
<211> LENGTH: 244
<212> TYPE: DNA
<213> ORGANISM: Artificial Sequence
<220> FEATURE:
<223> OTHER INFORMATION: Mutant terminator

<400> SEQUENCE: 10

```
agtaagagcg ctacattggt ctacctttt gttctactta aacattagtt agttcgtttt    60
cttttctca ttttttatg tttcccccc aaagtctga ttttataata ttttatttca      120
cacaattcca tttaacagag ggggaataga ttctttagct tagaaaatta gtgatcaata   180
tatatttgcc tttcttttca tcttttcagt gatattaatg gtttcgagac actgcaatgg   240
ccct                                                                244
```

<210> SEQ ID NO 11
<211> LENGTH: 244
<212> TYPE: DNA
<213> ORGANISM: Artificial Sequence
<220> FEATURE:
<223> OTHER INFORMATION: Mutant terminator

<400> SEQUENCE: 11

```
agtaagagcg ctacattggt ctacctttt gttcttttta aacattagtt agttcgtttt    60
cttttctca ttttttatg tttcccccc aaagtctga ttttataata ttttatttca      120
cacaattcca tttaacagag ggggaataga ttctttagct tagaaaatta gtgatcaata   180
tatatttgcc tttcttttca tcttttcagt gatattaatg gtttcgagac actgcaatgg   240
ccct                                                                244
```

<210> SEQ ID NO 12
<211> LENGTH: 244
<212> TYPE: DNA
<213> ORGANISM: Artificial Sequence
<220> FEATURE:
<223> OTHER INFORMATION: Mutant terminator

<400> SEQUENCE: 12

```
agtaagagcg ctacattggt ctacctttt gttctttac tacattagtt agttcgtttt    60
cttttctca ttttttatg tttcccccc aaagtctga ttttataata ttttatttca      120
cacaattcca tttaacagag ggggaataga ttctttagct tagaaaatta gtgatcaata   180
tatatttgcc tttcttttca tcttttcagt gatattaatg gtttcgagac actgcaatgg   240
ccct                                                                244
```

<210> SEQ ID NO 13
<211> LENGTH: 244

```
<212> TYPE: DNA
<213> ORGANISM: Artificial Sequence
<220> FEATURE:
<223> OTHER INFORMATION: Mutant terminator

<400> SEQUENCE: 13
agtaagagcg ctacattggt ctaccttttt gttcttttac ttaattagtt agttcgtttt    60 cttttctca ttttttatg tttccccccc aaagttctga ttttataata ttttatttca   120
cacaattcca tttaacagag ggggaataga ttctttagct tagaaaatta gtgatcaata   180
tatatttgcc tttcttttca tcttttcagt gatattaatg gtttcgagac actgcaatgg   240
ccct                                                                244

<210> SEQ ID NO 14
<211> LENGTH: 244
<212> TYPE: DNA
<213> ORGANISM: Artificial Sequence
<220> FEATURE:
<223> OTHER INFORMATION: Mutant terminator

<400> SEQUENCE: 14
agtaagagcg ctacattggt ctaccttttt gttcttttac ttaaacagtt agttcgtttt    60 cttttctca ttttttatg tttccccccc aaagttctga ttttataata ttttatttca   120
cacaattcca tttaacagag ggggaataga ttctttagct tagaaaatta gtgatcaata   180
tatatttgcc tttcttttca tcttttcagt gatattaatg gtttcgagac actgcaatgg   240
ccct                                                                244

<210> SEQ ID NO 15
<211> LENGTH: 244
<212> TYPE: DNA
<213> ORGANISM: Artificial Sequence
<220> FEATURE:
<223> OTHER INFORMATION: Mutant terminator

<400> SEQUENCE: 15
agtaagagcg ctacattggt ctaccttttt gttcttttac ttaaacatta agttcgtttt    60 cttttctca ttttttatg tttccccccc aaagttctga ttttataata ttttatttca   120
cacaattcca tttaacagag ggggaataga ttctttagct tagaaaatta gtgatcaata   180
tatatttgcc tttcttttca tcttttcagt gatattaatg gtttcgagac actgcaatgg   240
ccct                                                                244

<210> SEQ ID NO 16
<211> LENGTH: 244
<212> TYPE: DNA
<213> ORGANISM: Artificial Sequence
<220> FEATURE:
<223> OTHER INFORMATION: Mutant terminator

<400> SEQUENCE: 16
agtaagcgcg ctacattggt ctaccttttt gttcttttac ttaaacatta gtttcgtttt    60 cttttctca ttttttatg tttccccccc aaagttctga ttttataata ttttatttca   120
cacaattcca tttaacagag ggggaataga ttctttagct tagaaaatta gtgatcaata   180
tatatttgcc tttcttttca tcttttcagt gatattaatg gtttcgagac actgcaatgg   240
ccct                                                                244

<210> SEQ ID NO 17
```

```
<211> LENGTH: 244
<212> TYPE: DNA
<213> ORGANISM: Artificial Sequence
<220> FEATURE:
<223> OTHER INFORMATION: Mutant terminator

<400> SEQUENCE: 17
agtaagagcg ctacattggt ctacctttt gttcttttac ttaaacatta gttagttttt      60 cttttctca ttttttatg tttccccccc aaagttctga ttttataata ttttatttca     120
cacaattcca tttaacagag ggggaataga ttctttagct tagaaaatta gtgatcaata    180
tatatttgcc tttctttca tcttttcagt gatattaatg gtttcgagac actgcaatgg    240
ccct                                                                 244

<210> SEQ ID NO 18
<211> LENGTH: 244
<212> TYPE: DNA
<213> ORGANISM: Artificial Sequence
<220> FEATURE:
<223> OTHER INFORMATION: Mutant terminator

<400> SEQUENCE: 18
agtaagagcg ctacattggt ctacctttt gttcttttac ttaaacatta gttagttcgt      60 cttttctca ttttttatg tttccccccc aaagttctga ttttataata ttttatttca     120
cacaattcca tttaacagag ggggaataga ttctttagct tagaaaatta gtgatcaata    180
tatatttgcc tttctttca tcttttcagt gatattaatg gtttcgagac actgcaatgg    240
ccct                                                                 244

<210> SEQ ID NO 19
<211> LENGTH: 244
<212> TYPE: DNA
<213> ORGANISM: Artificial Sequence
<220> FEATURE:
<223> OTHER INFORMATION: Mutant terminator

<400> SEQUENCE: 19
agtaagagcg ctacattggt ctacctttt gttcttttac ttaaacatta gttagttcgt      60
ttttttctca ttttttatg tttccccccc aaagttctga ttttataata ttttatttca     120
cacaattcca tttaacagag ggggaataga ttctttagct tagaaaatta gtgatcaata    180
tatatttgcc tttctttca tcttttcagt gatattaatg gtttcgagac actgcaatgg    240
ccct                                                                 244

<210> SEQ ID NO 20
<211> LENGTH: 244
<212> TYPE: DNA
<213> ORGANISM: Artificial Sequence
<220> FEATURE:
<223> OTHER INFORMATION: Mutant terminator

<400> SEQUENCE: 20
agtaagagcg ctacattggt ctacctttt gttcttttac ttaaacatta gttagttcgt      60
tttcttctca ttttttatg tttccccccc aaagttctga ttttataata ttttatttca     120
cacaattcca tttaacagag ggggaataga ttctttagct tagaaaatta gtgatcaata    180
tatatttgcc tttctttca tcttttcagt gatattaatg gtttcgagac actgcaatgg    240
ccct                                                                 244
```

```
<210> SEQ ID NO 21
<211> LENGTH: 244
<212> TYPE: DNA
<213> ORGANISM: Artificial Sequence
<220> FEATURE:
<223> OTHER INFORMATION: Mutant terminator

<400> SEQUENCE: 21
agtaagagcg ctacattggt ctacctttt gttctttac ttaaacatta gttagttcgt      60
tttcttttca tttttttatg tttccccccc aaagttctga ttttataata ttttatttca     120
cacaattcca tttaacagag ggggaataga ttctttagct tagaaaatta gtgatcaata    180
tatatttgcc tttctttca tcttttcagt gatattaatg gtttcgagac actgcaatgg     240
ccct                                                                 244

<210> SEQ ID NO 22
<211> LENGTH: 244
<212> TYPE: DNA
<213> ORGANISM: Artificial Sequence
<220> FEATURE:
<223> OTHER INFORMATION: Mutant terminator

<400> SEQUENCE: 22
agtaagagcg ctacattggt ctacctttt gttctttac ttaaacatta gttagttcgt      60
tttctttttc tttttttatg tttccccccc aaagttctga ttttataata ttttatttca    120
cacaattcca tttaacagag ggggaataga ttctttagct tagaaaatta gtgatcaata    180
tatatttgcc tttctttca tcttttcagt gatattaatg gtttcgagac actgcaatgg     240
ccct                                                                 244

<210> SEQ ID NO 23
<211> LENGTH: 247
<212> TYPE: DNA
<213> ORGANISM: Artificial Sequence
<220> FEATURE:
<223> OTHER INFORMATION: Mutant terminator

<400> SEQUENCE: 23
agtaagagcg ctacattggt ctacctttt gttctttac ttaaacatta gttggttcgt      60
tttctttttc tcatttttt atgtttcccc cccaaagttc tgattttata atattttatt    120
tcacacaatt ccatttaaca gagggggaat agattctta gcttagaaaa ttagtgatca    180
atatatattt gcctttcttt tcatcttttc agtgatatta atggtttcga gacactgcaa   240
tggccct                                                              247

<210> SEQ ID NO 24
<211> LENGTH: 247
<212> TYPE: DNA
<213> ORGANISM: Artificial Sequence
<220> FEATURE:
<223> OTHER INFORMATION: Mutant terminator

<400> SEQUENCE: 24
agtaagagcg ctacattggt ctacctttt gttctttac ttaaacatta gttcgttcgt      60
tttctttttc tcatttttt atgtttcccc cccaaagttc tgattttata atattttatt    120
tcacacaatt ccatttaaca gagggggaat agattctta gcttagaaaa ttagtgatca    180
atatatattt gcctttcttt tcatcttttc agtgatatta atggtttcga gacactgcaa   240
tggccct                                                              247
```

<210> SEQ ID NO 25
<211> LENGTH: 247
<212> TYPE: DNA
<213> ORGANISM: Artificial Sequence
<220> FEATURE:
<223> OTHER INFORMATION: Mutant terminator

<400> SEQUENCE: 25

```
agtaagagcg ctacattggt ctaccttttt gttcttttac ttaaacatta gtttgttcgt    60
tttcttttc tcatttttt atgtttcccc cccaaagttc tgattttata atattttatt    120
tcacacaatt ccatttaaca gaggggaat agattcttta gcttagaaaa ttagtgatca    180
atatatattt gcctttcttt tcatcttttc agtgatatta atggtttcga gacactgcaa    240
tggccct                                                              247
```

<210> SEQ ID NO 26
<211> LENGTH: 247
<212> TYPE: DNA
<213> ORGANISM: Artificial Sequence
<220> FEATURE:
<223> OTHER INFORMATION: Mutant terminator

<400> SEQUENCE: 26

```
agtaagagcg ctacattggt ctaccttttt gttcttttac ttaaacatta gttaattcgt    60
tttcttttc tcatttttt atgtttcccc cccaaagttc tgattttata atattttatt    120
tcacacaatt ccatttaaca gaggggaat agattcttta gcttagaaaa ttagtgatca    180
atatatattt gcctttcttt tcatcttttc agtgatatta atggtttcga gacactgcaa    240
tggccct                                                              247
```

<210> SEQ ID NO 27
<211> LENGTH: 247
<212> TYPE: DNA
<213> ORGANISM: Artificial Sequence
<220> FEATURE:
<223> OTHER INFORMATION: Mutant terminator

<400> SEQUENCE: 27

```
agtaagagcg ctacattggt ctaccttttt gttcttttac ttaaacatta gttacttcgt    60
tttcttttc tcatttttt atgtttcccc cccaaagttc tgattttata atattttatt    120
tcacacaatt ccatttaaca gaggggaat agattcttta gcttagaaaa ttagtgatca    180
atatatattt gcctttcttt tcatcttttc agtgatatta atggtttcga gacactgcaa    240
tggccct                                                              247
```

<210> SEQ ID NO 28
<211> LENGTH: 247
<212> TYPE: DNA
<213> ORGANISM: Artificial Sequence
<220> FEATURE:
<223> OTHER INFORMATION: Mutant terminator

<400> SEQUENCE: 28

```
agtaagagcg ctacattggt ctaccttttt gttcttttac ttaaacatta gttatttcgt    60
tttcttttc tcatttttt atgtttcccc cccaaagttc tgattttata atattttatt    120
tcacacaatt ccatttaaca gaggggaat agattcttta gcttagaaaa ttagtgatca    180
atatatattt gcctttcttt tcatcttttc agtgatatta atggtttcga gacactgcaa    240
tggccct                                                              247
```

<210> SEQ ID NO 29
<211> LENGTH: 247
<212> TYPE: DNA
<213> ORGANISM: Artificial Sequence
<220> FEATURE:
<223> OTHER INFORMATION: Mutant terminator

<400> SEQUENCE: 29

```
agtaagagcg ctacattggt ctaccttttt gttcttttac ttaaacatta gttagatcgt      60
tttcttttc tcattttttt atgtttcccc cccaaagttc tgattttata atattttatt     120
tcacacaatt ccatttaaca gagggggaat agattcttta gcttagaaaa ttagtgatca     180
atatatattt gcctttcttt tcatcttttc agtgatatta atggtttcga gacactgcaa     240
tggccct                                                              247
```

<210> SEQ ID NO 30
<211> LENGTH: 247
<212> TYPE: DNA
<213> ORGANISM: Artificial Sequence
<220> FEATURE:
<223> OTHER INFORMATION: Mutant terminator

<400> SEQUENCE: 30

```
agtaagagcg ctacattggt ctaccttttt gttcttttac ttaaacatta gttaggtcgt      60
tttcttttc tcattttttt atgtttcccc cccaaagttc tgattttata atattttatt     120
tcacacaatt ccatttaaca gagggggaat agattcttta gcttagaaaa ttagtgatca     180
atatatattt gcctttcttt tcatcttttc agtgatatta atggtttcga gacactgcaa     240
tggccct                                                              247
```

<210> SEQ ID NO 31
<211> LENGTH: 247
<212> TYPE: DNA
<213> ORGANISM: Artificial Sequence
<220> FEATURE:
<223> OTHER INFORMATION: Mutant terminator

<400> SEQUENCE: 31

```
agtaagagcg ctacattggt ctaccttttt gttcttttac ttaaacatta gttagctcgt      60
tttcttttc tcattttttt atgtttcccc cccaaagttc tgattttata atattttatt     120
tcacacaatt ccatttaaca gagggggaat agattcttta gcttagaaaa ttagtgatca     180
atatatattt gcctttcttt tcatcttttc agtgatatta atggtttcga gacactgcaa     240
tggccct                                                              247
```

<210> SEQ ID NO 32
<211> LENGTH: 247
<212> TYPE: DNA
<213> ORGANISM: Artificial Sequence
<220> FEATURE:
<223> OTHER INFORMATION: Mutant terminator

<400> SEQUENCE: 32

```
agtaagagcg ctacattggt ctaccttttt gttcttttac ttaaacatta gttagtacgt      60
tttcttttc tcattttttt atgtttcccc cccaaagttc tgattttata atattttatt     120
tcacacaatt ccatttaaca gagggggaat agattcttta gcttagaaaa ttagtgatca     180
atatatattt gcctttcttt tcatcttttc agtgatatta atggtttcga gacactgcaa     240
```

```
tggccct                                                                    247

<210> SEQ ID NO 33
<211> LENGTH: 247
<212> TYPE: DNA
<213> ORGANISM: Artificial Sequence
<220> FEATURE:
<223> OTHER INFORMATION: Mutant terminator

<400> SEQUENCE: 33
agtaagagcg ctacattggt ctaccttttt gttcttttac ttaaacatta gttagtgcgt      60 tttcttttc tcattttttt atgtttcccc cccaaagttc tgattttata atattttatt     120
tcacacaatt ccatttaaca gagggggaat agattcttta gcttagaaaa ttagtgatca     180
atatatattt gcctttcttt tcatcttttc agtgatatta atggtttcga gacactgcaa     240
tggccct                                                                    247

<210> SEQ ID NO 34
<211> LENGTH: 247
<212> TYPE: DNA
<213> ORGANISM: Artificial Sequence
<220> FEATURE:
<223> OTHER INFORMATION: Mutant terminator

<400> SEQUENCE: 34
agtaagagcg ctacattggt ctaccttttt gttcttttac ttaaacatta gttagtccgt      60 tttcttttc tcattttttt atgtttcccc cccaaagttc tgattttata atattttatt     120
tcacacaatt ccatttaaca gagggggaat agattcttta gcttagaaaa ttagtgatca     180
atatatattt gcctttcttt tcatcttttc agtgatatta atggtttcga gacactgcaa     240
tggccct                                                                    247

<210> SEQ ID NO 35
<211> LENGTH: 247
<212> TYPE: DNA
<213> ORGANISM: Artificial Sequence
<220> FEATURE:
<223> OTHER INFORMATION: Mutant terminator

<400> SEQUENCE: 35
agtaagagcg ctacattggt ctaccttttt gttcttttac ttaaacatta gttagttagt      60 tttcttttc tcattttttt atgtttcccc cccaaagttc tgattttata atattttatt     120
tcacacaatt ccatttaaca gagggggaat agattcttta gcttagaaaa ttagtgatca     180
atatatattt gcctttcttt tcatcttttc agtgatatta atggtttcga gacactgcaa     240
tggccct                                                                    247

<210> SEQ ID NO 36
<211> LENGTH: 247
<212> TYPE: DNA
<213> ORGANISM: Artificial Sequence
<220> FEATURE:
<223> OTHER INFORMATION: Mutant terminator

<400> SEQUENCE: 36
agtaagagcg ctacattggt ctaccttttt gttcttttac ttaaacatta gttagttggt      60 tttcttttc tcattttttt atgtttcccc cccaaagttc tgattttata atattttatt     120
tcacacaatt ccatttaaca gagggggaat agattcttta gcttagaaaa ttagtgatca     180
atatatattt gcctttcttt tcatcttttc agtgatatta atggtttcga gacactgcaa     240
```

```
tggccct                                                               247

<210> SEQ ID NO 37
<211> LENGTH: 247
<212> TYPE: DNA
<213> ORGANISM: Artificial Sequence
<220> FEATURE:
<223> OTHER INFORMATION: Mutant terminator

<400> SEQUENCE: 37
agtaagagcg ctacattggt ctaccttttt gttcttttac ttaaacatta gttagtttgt    60 tttcttttc tcatttttt atgtttcccc cccaaagttc tgattttata atattttatt     120
tcacacaatt ccatttaaca gagggggaat agattcttta gcttagaaaa ttagtgatca   180
atatatattt gcctttcttt tcatcttttc agtgatatta atggtttcga gacactgcaa   240
tggccct                                                               247

<210> SEQ ID NO 38
<211> LENGTH: 247
<212> TYPE: DNA
<213> ORGANISM: Artificial Sequence
<220> FEATURE:
<223> OTHER INFORMATION: Mutant terminator

<400> SEQUENCE: 38
agtaagagcg ctacattggt ctaccttttt gttcttttac ttaaacatta gttagttcat    60 tttcttttc tcatttttt atgtttcccc cccaaagttc tgattttata atattttatt     120
tcacacaatt ccatttaaca gagggggaat agattcttta gcttagaaaa ttagtgatca   180
atatatattt gcctttcttt tcatcttttc agtgatatta atggtttcga gacactgcaa   240
tggccct                                                               247

<210> SEQ ID NO 39
<211> LENGTH: 247
<212> TYPE: DNA
<213> ORGANISM: Artificial Sequence
<220> FEATURE:
<223> OTHER INFORMATION: Mutant terminator

<400> SEQUENCE: 39
agtaagagcg ctacattggt ctaccttttt gttcttttac ttaaacatta gttagttcct    60 tttcttttc tcatttttt atgtttcccc cccaaagttc tgattttata atattttatt     120
tcacacaatt ccatttaaca gagggggaat agattcttta gcttagaaaa ttagtgatca   180
atatatattt gcctttcttt tcatcttttc agtgatatta atggtttcga gacactgcaa   240
tggccct                                                               247

<210> SEQ ID NO 40
<211> LENGTH: 247
<212> TYPE: DNA
<213> ORGANISM: Artificial Sequence
<220> FEATURE:
<223> OTHER INFORMATION: Mutant terminator

<400> SEQUENCE: 40
agtaagagcg ctacattggt ctaccttttt gttcttttac ttaaacatta gttagttctt    60 tttcttttc tcatttttt atgtttcccc cccaaagttc tgattttata atattttatt     120
tcacacaatt ccatttaaca gagggggaat agattcttta gcttagaaaa ttagtgatca   180
```

```
atatatattt gcctttcttt tcatcttttc agtgatatta atggtttcga gacactgcaa    240
tggccct                                                              247

<210> SEQ ID NO 41
<211> LENGTH: 247
<212> TYPE: DNA
<213> ORGANISM: Artificial Sequence
<220> FEATURE:
<223> OTHER INFORMATION: Mutant terminator

<400> SEQUENCE: 41
agtaagagcg ctacattggt ctacctttt gttcttttac ttaaacattg gttagttcgt    60 tttcttttc tcattttttt atgtttcccc cccaaagttc tgattttata atattttatt    120
tcacacaatt ccatttaaca gaggggaat agattctta gcttagaaaa ttagtgatca     180
atatatattt gcctttcttt tcatcttttc agtgatatta atggtttcga gacactgcaa    240
tggccct                                                              247

<210> SEQ ID NO 42
<211> LENGTH: 247
<212> TYPE: DNA
<213> ORGANISM: Artificial Sequence
<220> FEATURE:
<223> OTHER INFORMATION: Mutant terminator

<400> SEQUENCE: 42
agtaagagcg ctacattggt ctacctttt gttcttttac ttaaacattc gttagttcgt    60 tttcttttc tcattttttt atgtttcccc cccaaagttc tgattttata atattttatt    120
tcacacaatt ccatttaaca gaggggaat agattctta gcttagaaaa ttagtgatca     180
atatatattt gcctttcttt tcatcttttc agtgatatta atggtttcga gacactgcaa    240
tggccct                                                              247

<210> SEQ ID NO 43
<211> LENGTH: 247
<212> TYPE: DNA
<213> ORGANISM: Artificial Sequence
<220> FEATURE:
<223> OTHER INFORMATION: Mutant terminator

<400> SEQUENCE: 43
agtaagagcg ctacattggt ctacctttt gttcttttac ttaaacattt gttagttcgt    60 tttcttttc tcattttttt atgtttcccc cccaaagttc tgattttata atattttatt    120
tcacacaatt ccatttaaca gaggggaat agattctta gcttagaaaa ttagtgatca     180
atatatattt gcctttcttt tcatcttttc agtgatatta atggtttcga gacactgcaa    240
tggccct                                                              247

<210> SEQ ID NO 44
<211> LENGTH: 247
<212> TYPE: DNA
<213> ORGANISM: Artificial Sequence
<220> FEATURE:
<223> OTHER INFORMATION: Mutant terminator

<400> SEQUENCE: 44
agtaagagcg ctacattggt ctacctttt gttcttttac ttaaacatta attagttcgt    60 tttcttttc tcattttttt atgtttcccc cccaaagttc tgattttata atattttatt    120
tcacacaatt ccatttaaca gaggggaat agattctta gcttagaaaa ttagtgatca     180
```

```
atatatattt gcctttcttt tcatcttttc agtgatatta atggtttcga gacactgcaa    240
tggccct                                                              247

<210> SEQ ID NO 45
<211> LENGTH: 247
<212> TYPE: DNA
<213> ORGANISM: Artificial Sequence
<220> FEATURE:
<223> OTHER INFORMATION: Mutant terminator

<400> SEQUENCE: 45
agtaagagcg ctacattggt ctaccttttt gttcttttac ttaaacatta cttagttcgt     60 tttcttttc tcattttttt atgtttcccc cccaaagttc tgattttata atattttatt    120
tcacacaatt ccatttaaca gagggggaat agattcttta gcttagaaaa ttagtgatca    180
atatatattt gcctttcttt tcatcttttc agtgatatta atggtttcga gacactgcaa    240
tggccct                                                              247

<210> SEQ ID NO 46
<211> LENGTH: 247
<212> TYPE: DNA
<213> ORGANISM: Artificial Sequence
<220> FEATURE:
<223> OTHER INFORMATION: Mutant terminator

<400> SEQUENCE: 46
agtaagagcg ctacattggt ctaccttttt gttcttttac ttaaacatta tttagttcgt     60 tttcttttc tcattttttt atgtttcccc cccaaagttc tgattttata atattttatt    120
tcacacaatt ccatttaaca gagggggaat agattcttta gcttagaaaa ttagtgatca    180
atatatattt gcctttcttt tcatcttttc agtgatatta atggtttcga gacactgcaa    240
tggccct                                                              247

<210> SEQ ID NO 47
<211> LENGTH: 247
<212> TYPE: DNA
<213> ORGANISM: Artificial Sequence
<220> FEATURE:
<223> OTHER INFORMATION: Mutant terminator

<400> SEQUENCE: 47
agtaagagcg ctacattggt ctaccttttt gttcttttac ttaaacatta gatagttcgt     60 tttcttttc tcattttttt atgtttcccc cccaaagttc tgattttata atattttatt    120
tcacacaatt ccatttaaca gagggggaat agattcttta gcttagaaaa ttagtgatca    180
atatatattt gcctttcttt tcatcttttc agtgatatta atggtttcga gacactgcaa    240
tggccct                                                              247

<210> SEQ ID NO 48
<211> LENGTH: 247
<212> TYPE: DNA
<213> ORGANISM: Artificial Sequence
<220> FEATURE:
<223> OTHER INFORMATION: Mutant terminator

<400> SEQUENCE: 48
agtaagagcg ctacattggt ctaccttttt gttcttttac ttaaacatta ggtagttcgt     60 tttcttttc tcattttttt atgtttcccc cccaaagttc tgattttata atattttatt    120
```

```
tcacacaatt ccatttaaca gagggggaat agattcttta gcttagaaaa ttagtgatca      180
atatatattt gcctttcttt tcatcttttc agtgatatta atggtttcga gacactgcaa      240
tggccct                                                                247

<210> SEQ ID NO 49
<211> LENGTH: 247
<212> TYPE: DNA
<213> ORGANISM: Artificial Sequence
<220> FEATURE:
<223> OTHER INFORMATION: Mutant terminator

<400> SEQUENCE: 49
agtaagagcg ctacattggt ctaccttttt gttcttttac ttaaacatta gctagttcgt       60 tttcttttc tcattttttt atgtttcccc cccaaagttc tgattttata atattttatt      120
tcacacaatt ccatttaaca gagggggaat agattcttta gcttagaaaa ttagtgatca      180
atatatattt gcctttcttt tcatcttttc agtgatatta atggtttcga gacactgcaa      240
tggccct                                                                247

<210> SEQ ID NO 50
<211> LENGTH: 247
<212> TYPE: DNA
<213> ORGANISM: Artificial Sequence
<220> FEATURE:
<223> OTHER INFORMATION: Mutant terminator

<400> SEQUENCE: 50
agtaagagcg ctacattggt ctaccttttt gttcttttac ttaaacatta gtaagttcgt       60 tttcttttc tcattttttt atgtttcccc cccaaagttc tgattttata atattttatt      120
tcacacaatt ccatttaaca gagggggaat agattcttta gcttagaaaa ttagtgatca      180
atatatattt gcctttcttt tcatcttttc agtgatatta atggtttcga gacactgcaa      240
tggccct                                                                247

<210> SEQ ID NO 51
<211> LENGTH: 247
<212> TYPE: DNA
<213> ORGANISM: Artificial Sequence
<220> FEATURE:
<223> OTHER INFORMATION: Mutant terminator

<400> SEQUENCE: 51
agtaagagcg ctacattggt ctaccttttt gttcttttac ttaaacatta gtgagttcgt       60 tttcttttc tcattttttt atgtttcccc cccaaagttc tgattttata atattttatt      120
tcacacaatt ccatttaaca gagggggaat agattcttta gcttagaaaa ttagtgatca      180
atatatattt gcctttcttt tcatcttttc agtgatatta atggtttcga gacactgcaa      240
tggccct                                                                247

<210> SEQ ID NO 52
<211> LENGTH: 247
<212> TYPE: DNA
<213> ORGANISM: Artificial Sequence
<220> FEATURE:
<223> OTHER INFORMATION: Mutant terminator

<400> SEQUENCE: 52
agtaagagcg ctacattggt ctaccttttt gttcttttac ttaaacatta gtcagttcgt       60 tttcttttc tcattttttt atgtttcccc cccaaagttc tgattttata atattttatt      120
```

-continued

```
tcacacaatt ccatttaaca gaggggaat agattcttta gcttagaaaa ttagtgatca       180
atatatattt gcctttcttt tcatcttttc agtgatatta atggtttcga gacactgcaa       240
tggccct                                                                  247
```

<210> SEQ ID NO 53
<211> LENGTH: 241
<212> TYPE: DNA
<213> ORGANISM: Artificial Sequence
<220> FEATURE:
<223> OTHER INFORMATION: Mutant terminator

<400> SEQUENCE: 53

```
agtaagagcg ctacattggt ctaccttttt cttttactta aacattagtt agttcgtttt        60
cttttctttt ttttatgttt cccccccaaa gttctgattt tataatattt tatttcacac       120
aattccattt aacagagggg gaatagattc tttagcttag aaaattagtg atcaatatat       180
atttgccttt cttttcatct tttcagtgat attaatggtt tcgagacact gcaatggccc       240
t                                                                        241
```

<210> SEQ ID NO 54
<211> LENGTH: 241
<212> TYPE: DNA
<213> ORGANISM: Artificial Sequence
<220> FEATURE:
<223> OTHER INFORMATION: Mutant terminator

<400> SEQUENCE: 54

```
agtaagagcg ctacattggt ctaccttttt cttttactta aacattaatt agttcgtttt        60
cttttctttt ttttatgttt cccccccaaa gttctgattt tataatattt tatttcacac       120
aattccattt aacagagggg gaatagattc tttagcttag aaaattagtg atcaatatat       180
atttgccttt cttttcatct tttcagtgat attaatggtt tcgagacact gcaatggccc       240
t                                                                        241
```

YEAST TERMINATOR AND USE THEREFOR

TECHNICAL FIELD

The present description relates to a yeast terminator for increasing the expression level of a target gene, and to a use therefor.

DESCRIPTION OF RELATED ART

In budding yeasts, the PGK1 terminator and CYC1 terminator are commonly used downstream from target genes coding for target proteins and the like. Techniques have been reported for identifying terminator regions that increase expression by twice that obtained with these common terminators, and increasing the protein yields of target genes by disposing highly active terminators downstream from the coding regions of the target genes (Japanese Patent Application Publication No. 2014-39533, Yamanishi M, Ito Y, Kintaka R, Imamura C, Katahira S, Ikeuchi A, Moriya H, Matsuyama T. A genome-wide activity assessment of terminator regions in *Saccharomyces cerevisiae* provides a "terminatome" toolbox. ACS Synth Biol, 2, 337-347).

A detailed investigation of the properties of the top five reported highly-active terminators has revealed that the DIT1 terminator is the most active (Ito Y, Yamanishi M, Ikeuchi A, Imamura C, Tokuhiro K, Kitagawa T, Matsuyama T. Characterization of five terminator regions that increase the protein yield of a transgene in *Saccharomyces cerevisiae*. J Biotechnol, 168, 486-492). Because terminators and promoters act synergistically, the DIT1 terminator, which is the most active, should be broadly applicable to the metabolic engineering of budding yeasts in the same way as the high-expression TDH3 promoter and the like.

BRIEF SUMMARY OF INVENTION

When using metabolic engineering techniques to develop a recombinant yeast that produces a target substance, it is necessary to cause strong expression of a protein produced by a target gene. By enhancing the ability of a terminator to increase the produced amount of the protein, it should be possible to greatly reduce development costs by reducing the number of introduced copies of the target gene because more of the protein is produced per copy of the target gene. Moreover, if more of the protein is produced per molecule of mRNA, it should be possible to increase the quantity and yield of the final product because the energy used in mRNA synthesis and decomposition is directed to the target metabolic pathway.

The DIT1 terminator of budding yeasts is considered to be an effective means of achieving this object because it has the greatest effect on production of proteins produced by upstream gene coding regions. However, the wild-type DIT1 terminator has a naturally evolved nucleotide sequence and may not be optimal for maximizing production of a protein produced by an introduced upstream gene.

The present description provides a yeast terminator having greater capability than the wild-type DIT1 terminator, together with a use therefor.

The inventors of the present invention introduced mutations into the nucleotide sequence of a DIT1 terminator region identified by the inventors, and into a presumed cis-sequence contained in this region and before and after the cis-sequence, and the activities of the modified DIT1 terminators were evaluated by evaluation methods developed by the inventors. As a result, they were able to obtain yeast terminators that were more active even than the DIT1 terminator. The present description provides the following means based on these findings.

(1) A yeast terminator derived from a yeast DIT1 terminator, wherein the yeast terminator, when aligned with the nucleotide sequence represented by SEQ ID NO: 1, comprises a partial nucleotide sequence corresponding to the partial nucleotide sequence AGTTCG of positions 54 to 59 in the nucleotide sequence represented by SEQ ID NO:1, and also comprises one or two or more mutations selected from the group consisting of (a) to (c) below:

(a) a first mutation substituting TTTTTCT for the partial nucleotide sequence TTTTGTTCT of positions 27 to 35 in the nucleotide sequence represented by SEQ ID NO:1;

(b) a second mutation substituting TCTTTT for the partial nucleotide sequence TCTCATTTT of positions 69 to 77 in the nucleotide sequence represented by SEQ ID NO:1; and (c) a third mutation substituting A for the G of position 51 in the nucleotide sequence represented by SEQ ID NO:1.

(2) The yeast terminator according to (1), comprising the first mutation.

(3) The yeast terminator according to (1) or (2), comprising the second mutation.

(4) The yeast terminator according to any one of (1) to (3), comprising the third mutation.

(5) The yeast terminator according to (1), comprising the first mutation and the second mutation.

(6) The yeast terminator according to (1), comprising the first mutation, the second mutation and the third mutation.

(7) The yeast terminator according to any one of (1) to (6), comprising a nucleotide sequence corresponding to the partial nucleotide sequence of positions 1 to 26 in the nucleotide sequence represented by SEQ ID NO:1 when aligned with that nucleotide sequence.

(8) The yeast terminator according to any one of (1) to (7), comprising a nucleotide sequence corresponding to the partial nucleotide sequence TAAACATTA of positions 42 to 50 in the nucleotide sequence represented by SEQ ID NO:1 when aligned with that nucleotide sequence.

(9) The yeast terminator according to any one of (1) to (8), comprising a nucleotide sequence corresponding to the partial nucleotide sequence TTTTCTTTT of positions 60 to 68 of the nucleotide sequence represented by SEQ ID NO:1 when aligned with that nucleotide sequence.

(10) The yeast terminator according to any one of (1) to (9), wherein a nucleotide sequence corresponding to the partial nucleotide sequence of positions 78 to 205 in the nucleotide sequence represented by SEQ ID NO:1 when aligned with that nucleotide sequence has 90% or more identity with that partial nucleotide sequence.

(11) A cassette for gene expression in yeasts, the cassette comprising: a promoter region; a cloning site for introducing a coding region of a target gene or the coding region of the target gene; and a terminator region containing the yeast terminator according to any one of (1) to (10).

(12) A vector for gene expression in yeasts, the vector comprising: a promoter region; a cloning site for introducing a coding region of a target gene or the coding region of the target gene; and a terminator region containing the yeast terminator according to any one of (1) to (10).

(13) A recombinant yeast carrying: a promoter region; a coding region of a target gene; and a terminator region containing the yeast terminator according to any one of (1) to (10).

(14) A method for producing a substance using a yeast, comprising a step of culturing the recombinant yeast according to (13).

DETAILED DESCRIPTION OF INVENTION

Figure 1:
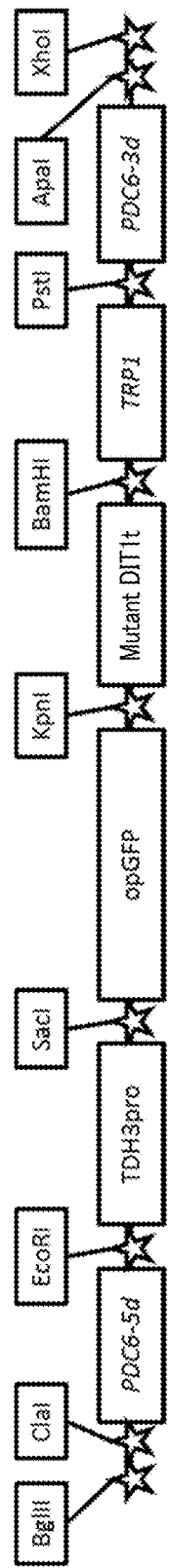
FIG. 1 shows the structure of a mutant DIT1 terminator genome insertion construct, with the restriction enzyme sites shown above.
Figure 2:
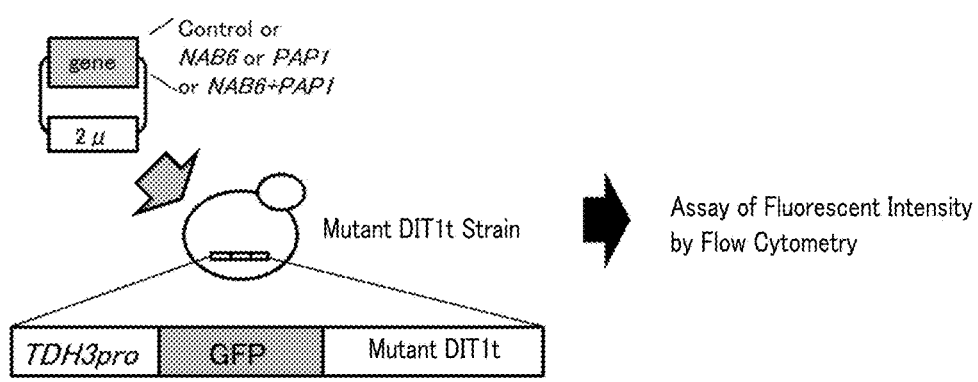
FIG. 2 shows an outline of a NAB6-PAP1 assay.

The disclosures of this description relate to a yeast terminator and a use therefor. With the yeast terminator disclosed in this description, an exogenous gene or other desired target gene can be expressed in a yeast with even greater expression-enhancing activity in comparison with the DIT1 terminator, which has more than twice the expression-enhancing activity of the PGK1 terminator.

(Yeast Terminator)

The yeast terminator disclosed in this description (hereunder called the yeast terminator of the invention) is a yeast terminator derived from a yeast DIT1 terminator, and has one or two or more mutations selected from the group consisting of (a) to (c) below in an alignment with the nucleotide sequence represented by SEQ ID NO:1:

(a) a first mutation substituting TTTTTCT for the partial nucleotide sequence TTTTGTTCT of positions 27 to 35 in the nucleotide sequence represented by SEQ ID NO:1;

(b) a second mutation substituting TCTTTT for the partial nucleotide sequence TCTCATTTT of positions 69 to 77 in the nucleotide sequence represented by SEQ ID NO:1; and (c) a third mutation substituting A for the G of position 51 in the nucleotide sequence represented by SEQ ID NO:1.

The yeast terminator of the invention is derived from a yeast DIT1 gene terminator. "Derived from a yeast DIT1 gene terminator" here means derived from a DIT1 gene terminator of a naturally occurring yeast, that is, from a region of preferably 150 nucleotides, or more preferably 180 nucleotides, or still more preferably 200 nucleotides, or yet more preferably 210 nucleotides, or even more preferably 230 nucleotides, or especially 250 nucleotides following the stop codon of a protein coding region of a DIT1 gene, or from a region obtained by modifying such a region. Consequently, this may be either a natural terminator of a naturally occurring DIT1 gene or a non-natural terminator obtained by artificial modification of a natural DIT1 gene terminator, as long as it has the mutations described above in the nucleotide sequence represented by SEQ ID NO:1.

Moreover, the yeast terminator of the invention may be either naturally obtained DNA, or may have been prepared using natural DNA, or may have been entirely artificially synthesized by genetic engineering or chemical synthesis techniques, as long as it has one or two or more of the features described below in its nucleotide sequence and is derived from a yeast DIT1 gene terminator.

The yeast terminator of the invention preferably has gene expression enhancing activity greater than that of a wild-type DIT1 terminator consisting of the nucleotide sequence represented by SEQ ID NO:1. Preferably, its relative activity is at least 1.1 times, or more preferably at least 1.2 times, or still more preferably at least 1.3 times, or yet more preferably at least 1.4 times, or even more preferably at least 1.5 times the gene expression activity of that wild-type terminator.

Relative activity in comparison with the wild-type DIT1 terminator can be evaluated by the methods described below for example.

(Core Sequence)

When aligned with the nucleotide sequence represented by SEQ ID NO:1, the yeast terminator of the invention preferably has a nucleotide sequence corresponding to the partial nucleotide sequence AGTTCG (also called the core sequence in this description) of positions 54 to 59 in the nucleotide sequence represented by SEQ ID NO:1. Expression enhancing activity based on NAB6-PAP1 activation can be retained by retaining this core sequence. The partial nucleotide sequence of positions 52 to 53 may also be maintained in addition to the core sequence.

Mutations and the like that may be provided to the nucleotide sequence represented by SEQ ID NO:1 in the yeast terminator of the invention are explained below.

(First Mutation)

The first mutation that can be provided in the yeast terminator of the invention is a mutation substituting TTTTCT for the partial nucleotide sequence TTTTGTTCT of positions 27 to 35 in the nucleotide sequence represented by SEQ ID NO:1 in an alignment of the nucleotide sequence of the yeast terminator of the invention with the nucleotide sequence represented by SEQ ID NO:1.

In this description, nucleotide sequence alignment can be accomplished using various known programs. Examples of such programs include BLAST (blast.ncbi.nlm.nih.gov/Blast.cgi), COBALT (www.st-va.ncbi.nlm.nih.gov/tools/cobalt/re_cobalt.cgi), Clustal W (www.genome.jp/tools/clustalw/), Clustal Omega (www.ebi.ac.uk/Tools/msa/clustalo/) and MUSCLE (www.ebi.ac.uk/Tools/msa/muscle), and other programs that are available commercially. Using an alignment program obtained from a public website such as NCBI, NIH, DDBJ or EBI, or using a program on such a website, or using a commercially available program, a person skilled in the art can align a nucleotide sequence for comparison against the nucleotide sequence represented by SEQ ID NO:1. By such alignment, it is possible to specify what nucleotides or nucleotide sequences are present in the nucleotide sequence for comparison when compared with a corresponding partial nucleotide sequence consisting of one or two or more nucleotides in the nucleotide sequence represented by SEQ ID NO:1.

The first mutation in the yeast terminator of the invention is a mutation that results in the deletion of 3 nucleotides out of positions 27 to 35 in the nucleotide sequence represented by SEQ ID NO:1. The configuration of the mutation as represented by the alignment program is not particularly limited as long as the first mutation can be identified by alignment of the nucleotide sequence of the yeast terminator with the nucleotide sequence represented by SEQ ID NO:1. This is because the alignment results may be presented differently depending on the program, the sequence, the parameters and the like.

(Second Mutation)

The second mutation that can be provided in the yeast terminator of the invention is a mutation substituting TCTTTT for the partial nucleotide sequence TCTCATTTT of positions 69 to 77 in the nucleotide sequence represented by SEQ ID NO:1 in an alignment of the nucleotide sequence of the yeast terminator of the invention with the nucleotide sequence represented by SEQ ID NO:1.

The second mutation in the yeast terminator of the invention is a mutation that results in the deletion of 3 nucleotides out of positions 69 to 77 in the nucleotide sequence represented by SEQ ID NO:1. As in the case of the first mutation, the configuration of the mutation as represented by the alignment program is not particularly limited as long as the second mutation can be identified by alignment of the nucleotide sequence of the yeast terminator with the nucleotide sequence represented by SEQ ID NO:1.

(Third Mutation)

The third mutation that can be provided in the yeast terminator of the invention is a substitution mutation substituting A for the G of position 51 in the nucleotide sequence represented by SEQ ID NO:1 in an alignment of the nucleotide sequence of the yeast terminator of the invention with the nucleotide sequence represented by SEQ ID NO:1.

Giving the yeast terminator of the invention one, two or all three of the first mutation, the second mutation and the third mutation described above in an alignment with the nucleotide sequence represented by SEQ ID NO:1 gives the yeast terminator greater expression enhancing activity than a wild-type DIT1 terminator having the nucleotide sequence represented by SEQ ID NO:1.

For example, giving the yeast terminator of the invention the first mutation can give it at least 1.1 times the expression enhancing activity of the wild-type terminator and at least 2.8 times the expression enhancing activity of the PGK1 terminator. Moreover, for example giving the yeast terminator of the invention the second mutation can give it at least 1.2 times the expression enhancing activity of the wild-type terminator and at least 3.0 times the expression enhancing activity of the PGK1 terminator. Also, for example giving the yeast terminator of the invention the first mutation and the second mutation can give it at least about 1.5 times the expression enhancing activity of the wild-type terminator and at least about 4.0 times the expression enhancing activity of the PGK1 terminator. Giving the yeast terminator of the invention the first mutation, the second mutation and the third mutation can give it at least about 1.5 times the expression enhancing activity of the wild-type terminator and at least 4.0 times the expression enhancing activity of the PGK1 terminator. Moreover, for example giving the yeast terminator of the invention the second mutation can also give it at least 1.4 times the expression enhancing activity of the wild-type terminator and at least 4.0 times the expression enhancing activity of the PGK1 terminator.

To obtain expression enhancing activity, in yeasts, a construct having a GFP coding gene introduced under the control of a TDH3 promoter, with the wild-type terminator, the PGK1 terminator or the wild-type terminator and the yeast terminator of the invention attached downstream therefrom, is introduced for example into the PDC6 gene locus of a wild-type yeast such as W303-1a (*Saccharomyces cerevisiae*) to obtain a transformant. The expression-enhancing activities of the various yeast terminators relative to those of the wild-type terminator and PGK1 terminator can then be obtained by growing the various yeasts through the logarithmic growth phase up to the stationary phase, and measuring GFP fluorescence. The expression enhancing activity is the maximum expression enhancing activity observed during the stationary phase.

Expression enhancing activity is preferably obtained as relative activity given 1 as the expression enhancing activity obtained with the PGK1 terminator.

The yeast terminator of the invention may also comprise the following partial sequences in addition to the aforementioned core sequence and first through third mutations. In an alignment with the nucleotide sequence represented by SEQ ID NO:1, for example, this yeast group preferably comprises the partial nucleotide sequence AGT AAG AGC GCT ACA TTG GTC TAC CT (hereunder sometimes called the first partial sequence) of positions 1 to 26 in the nucleotide sequence represented by SEQ ID NO:1. Expression enhancing activity can be retained by retaining this partial nucleotide sequence. As long as the resulting terminator activity is greater than that of a terminator consisting of the nucleotide sequence represented by SEQ ID NO:1, the terminator may also comprise a nucleotide sequence having preferably at least 90%, or more preferably at least 93%, or still more preferably at least 95%, or yet more preferably at least 97%, or even more preferably 100% identity with this partial nucleotide sequence.

In an alignment with the nucleotide sequence represented by SEQ ID NO:1, for example, the yeast terminator of the invention also preferably comprises a nucleotide sequence (hereunder called the second partial sequence) corresponding to the partial nucleotide sequence TAAACATTA of positions 42 to 50 in the nucleotide sequence represented by SEQ ID NO:1. Expression enhancing activity can be retained by retaining this partial nucleotide sequence. It may also comprise an additional nucleotide sequence corresponding to the partial nucleotide sequence of positions 36 to 41 in the nucleotide sequence represented by SEQ ID NO:1.

In an alignment with the nucleotide sequence represented by SEQ ID NO:1 for example, the yeast terminator of the invention also preferably comprises a nucleotide sequence (hereunder sometimes called the third partial sequence) corresponding to the partial nucleotide sequence TTTTCTTTT of positions 60 to 68 in the nucleotide sequence represented by SEQ ID NO:1. Expression enhancing activity can be retained by retaining this partial nucleotide sequence.

Moreover, in an alignment with the nucleotide sequence represented by SEQ ID NO: 1, the yeast terminator of the invention may also comprise the partial nucleotide sequence of positions 78 to 205 (hereunder sometimes called the fourth partial sequence) in the nucleotide sequence represented by SEQ ID NO:1. Expression enhancing activity can be retained by retaining this partial nucleotide sequence. As long as the resulting terminator activity is greater than that of a terminator consisting of the nucleotide sequence represented by SEQ ID NO:1, the terminator may also comprise a nucleotide sequence having preferably at least 85%, or more preferably at least 90%, or still more preferably at least 95%, or yet more preferably at least 96%, or even more preferably at least 97%, or especially 98%, or most preferably at least 99%, or ideally 100% identity with this partial nucleotide sequence.

The yeast terminator of the invention preferably comprises an added stop codon that functions in yeasts at the 5'-end of the nucleotide sequence represented by SEQ ID NO:1. Examples of stop codons include TAA, TAG and TGA. For example, TAA may be used.

The yeast terminator of the invention may be provided with only one or two or more selected from the first mutation, the second mutation and the third mutation in the nucleotide sequence of the wild-type terminator, but in an alignment with the nucleotide sequence represented by SEQ ID NO: 1, other mutations may also be included as long as they do not reduce the terminator activity.

For example, in an alignment with the nucleotide sequence represented by SEQ ID NO:1, the yeast terminator of the invention may be one that has preferably at least 85%, or more preferably at least 90%, or still more preferably at least 95% identity with the nucleotide sequence represented by SEQ ID NO:1 in at least a nucleotide sequence that does not contain either the core sequence or a partial nucleotide sequence corresponding to the first, second or third mutation, and that has greater expression enhancing activity than the wild-type terminator. Moreover, for example the yeast terminator of the invention has preferably at least 96%, or more preferably at least 97%, or still more preferably at least 98%, or yet more preferably at least 99% identity.

Moreover, in an alignment with the nucleotide sequence represented by SEQ ID NO:1, the yeast terminator of the invention may be one that has preferably at least 85%, or more preferably at least 90%, or still more preferably at least 95% identity with the nucleotide sequence represented by SEQ ID NO:1 in a nucleotide sequence that does not contain the core sequence, the first, second or third mutation or a nucleotide sequence corresponding to one or two or more partial nucleotide sequences selected from the first, second, third and fourth partial nucleotide sequence, and that has greater expression enhancing activity than the wild-type terminator. Moreover, for example the yeast terminator of the invention has preferably at least 96%, or more preferably at least 97%, or still more preferably at least 98%, or yet more preferably at least 99% identity.

"Identity" and "similarity" herein, as have been known well to those skilled in the art, are relationships between two or more proteins or two more polynucleotide determined by comparing the sequences. "Identity" in the art, also means the degree of sequence invariance between protein or polynucleotide sequences, as determined by the alignment between the protein or polynucleotide sequences, as the case maybe the alignment between strings of such sequences. In addition, "similarity" means the degree of sequence relatedness between protein or polynucleotide sequences, as determined by the alignment between the protein or polynucleotide sequences, as the case maybe the alignment between strings of such sequences. More specifically, "Similarity" is determined by the sequence identity or conservativeness (replacement which can maintain the physical and chemical properties of a particular amino acid or amino acid sequence). "Similarity" is referred to as similarity in the search result BLAST sequence homology to be described later. Preferred methods of determining "identity" or "similarity" are designed to give the longest alignment between the sequences to be tested. Method for determining identity and similarity, are codified in publicly available computer programs. "Identity" and "similarity" can be determined by, for example, using the BLAST (Basic Local Alignment Search Tool) program by Altschul et. al., (for example, Altschul S F, Gish W, Miller W, Myers E W, Lipman D J, J. Mol Biol, 215: P403-410 (1990), Altschyl S F, Madden T L, Schaffer A A, Zhang J, Miller W, Lipman D J, 25 Nucleic Acids Res. 25: p 3389-3402 (1997)). Where software such as BLAST used, it is but not limited to, preferable to use default values.

"Identity" is defined as a value obtained by dividing the same amino acid number by the total amino acid number and multiplying by 100 values. If the sequences in alignment are of different lengths (by gap or extension), the length of the longest sequence is used in the calculation.

The yeast terminator of the invention can also be hybridized under high-stringency conditions with a nucleic acid probe consisting of the nucleotide sequence represented by SEQ ID NO:1. The stringency of the hybridization reaction can be readily determined by a person skilled in the art, and is normally an empirical calculation dependent upon probe length, washing temperature and salt concentration. In general, longer probes require higher temperatures for proper annealing, while shorter probes require lower temperatures. Hybridization generally depends on the ability of denatured DNA to re-anneal when complementary strands are present in an environment below their melting temperature. The higher the degree of desired homology between the probe and a hybridizable sequence, the higher the relative temperature that can be used. As a result, a higher relative temperature tends to make the reaction conditions more stringent, and a lower temperature tends to make them less stringent. More details and explanations regarding stringency in hybridization reactions can be found in Ausubel et al., "Current Protocols in Molecular Biology", Wiley Interscience Publishers (1995).

"High stringency conditions", as defined in this description, signify conditions that: (1) employ a low ionic strength and high temperature for washing, such as for example, 0.015 M sodium chloride/0.0015 M sodium citrate/0.1% SDS at 50° C.; (2) employ a denaturing agent such as formamide during hybridization, for example, 50% (v/v) formamide with 50 mM sodium phosphate buffer (pH 6.5)/ 0.1% polyvinylpyrrolidone/0.1% Ficol/0.1% BSA with 750 mM sodium chloride/50 mM sodium citrate at 42° C.; or (3) involve washing at 42° C. in 0.2×SSC and at 55° C. in 50% formamide, followed by a high-stringency wash consisting of 0.1×SSC containing EDTA at 55° C., and also employ a solution of 50% formamide, 5×SSC, 50 mM sodium phosphate (pH 6.8), 0.1% sodium pyrophosphate, 5×Denhardt's solution, sonicated salmon sperm (50 µg/ml), 0.1% SDS, and 10% dextran sulfate at 42° C.

The yeast terminator of the invention may also have one or two or more nucleotides substituted, deleted and/or inserted in a part other than the first mutation, the second mutation and the third mutation in the nucleotide sequence represented by SEQ ID NO:1. The total number of such nucleotide substitutions, deletion and insertions is preferably not more than 30, or more preferably not more than 25, or still more preferably not more than 22, or yet more preferably not more than 20, or even more preferably not more than 17, or most preferably not more than 15, or especially not more than 12, or more especially not more than 10, or still more especially not more than 7, or yet more especially not more than 5, or even more especially not more than 3, or most especially not more than 2, or ideally not more than 1.

Examples of such yeast terminator of the invention include the respective nucleotide sequences represented by SEQ ID NO:2 (containing first mutation), SEQ ID NO:3 (containing second mutation), SEQ ID NO:4 (containing third mutation), SEQ ID NO:5 (containing first mutation and second mutation) and SEQ ID NO:6 (containing first mutation, second mutation and third mutation).

As explained above, the yeast terminator of the invention has even greater expression enhancing activity than the DIT1 terminator, which itself has superior expression enhancing activity in yeasts. Consequently, it has the ability to regulate the expression of useful genes more strongly in yeasts, and to regulate the expression of a wider range of useful genes.

(Gene Expression Cassette)

The gene expression cassette disclosed in this description (hereunder called the gene expression cassette of the invention) may comprise a promoter region that acts in yeasts, a cloning site for introducing a target gene coding region or the target gene coding region, and a terminator region containing the yeast terminator of the invention. With such a gene expression cassette, it is possible to strongly enhance the expression of a target gene in a yeast.

The promoter region that acts in yeasts is not particularly limited. Various known yeast promoters may be included appropriately. A common high-expression promoter such as a TDH1 promoter or an ADH1 promoter, TPI1 promoter, HXIT7 promoter, PGK1 promoter or the like may be selected appropriately as the yeast promoter.

The cloning site for introducing the target gene coding region may comprise one or two or more restriction enzyme sites for example. Such a cloning site may be constructed as necessary to include one or two or more desired restriction enzyme sites, or a commercial plasmid or vector may be adopted appropriately.

The target gene in the target gene coding region may be derived from any organism as long as it is designed to be expressed in yeasts. The target gene may be a natural gene coding for a naturally occurring protein, or a gene coding for a protein obtained by artificially modifying the amino acid sequence of a naturally occurring protein, or a gene coding for a fused protein obtained by fusing heterogeneous proteins for example. The target gene may also have been modified for codon usage in the yeast. Embodiments of the target gene are discussed below.

The terminator region contains the yeast terminator of the invention. The yeast terminator of the invention may be provided downstream from the stop codon of the target gene coding region. For example, it may be ligated directly to the stop codon.

The gene expression cassette of the invention may also comprise one or two or more restriction enzyme sites each at the 3'-end of the promoter region and the 5'-end of the terminator region that can be used to modify the gene expression cassette itself.

The gene expression cassette of the invention may also comprise homologous recombination regions for one or two or more yeast genes, for purposes of incorporating the gene expression cassette of the invention into a yeast chromosome. Yeast genes or regions that are less affected by gene disruption on the yeast chromosome are selected as the homologous recombination regions, and these regions are not particularly limited, but examples include the PDC6 gene and the like. For example, the homologous recombination regions may be regions homologous to an area upstream from a coding region and an area downstream from a coding region in a gene region on a yeast chromosome, and the length thereof is not particularly limited by is normally hundreds of nucleotides.

The gene expression cassette of the invention may also be provided with a selection marker gene for selecting a transformed yeast having the gene expression cassette of the invention introduced therein. Examples of selection marker genes include auxotrophic genes, drug resistance genes and the like. Such selection marker genes are themselves configured to be expressible.

(Expression Vector)

The vector for gene expression in yeasts disclosed in this description (hereunder sometimes called the vector of the invention) may comprise a promoter region, a cloning site for introducing a target gene coding region or the target gene coding region, and a terminator region containing the yeast terminator of the invention. In addition to the various embodiments explained above with respect to the gene expression cassette of the invention, the various embodiments described explained above with reference to the yeast terminator of the invention may be applied appropriately the promoter, cloning site, target gene coding region and terminator region. The vector of the invention may also comprise the gene expression cassette of the invention. Consequently, the vector of the invention may also comprise homologous recombination regions or a selection marker gene or the like as necessary.

(Recombinant Yeast)

The yeast disclosed in this description may carry a promoter region, a target gene coding region, and a terminator region containing the yeast terminator of the invention. With this yeast it is possible to enhance expression of a desired target gene.

This yeast can be obtained by introducing the gene expression cassette of the invention or the vector of the invention explained above into a yeast to transform the yeast.

Various known yeasts may be used as the yeast, and examples include *Saccharomyces cerevisiae* and other *Saccharomyces* yeasts, *Schizosaccharomyces pombe* and other *Schizosaccharomyces* yeasts, *Candida shehatae* and other *Candida* yeasts, *Pichia stipitis* and other *Pichia* yeasts, Hansenula yeasts, Kloeckera yeasts, Schwanniomyces yeasts and Yarrowia yeasts, Trichosporon yeasts, Brettanomyces yeasts, Pachysolen yeasts, Yamadazyma yeasts, Kluyveromyces marxianus, Kluyveromyces lactis and other Klauyveromyces yeasts, and Issatchenkia orientalis and other Issatchenkia yeasts. For purposes of industrial production for example, desirable examples include Saccharomyces cerevisiae, Saccharomyces pombe, Candida albicans, Pichia pastoris and Kluyveromyces lactis. Saccharomyces cerevisiae and Kluyveromyces lactis are particularly desirable.

Not only can expression of a desired target gene be controlled by the yeast terminator of the invention, but the yeast of the invention may also be provided with an enhancement system that further activates the terminator of the invention so as to further enhance expression of the desired target gene. This system may be for example an expression system such as that disclosed in Japanese Patent Application Publication No. 2015-136303, which is designed to enhance the expression of one or two or more genes selected from the group consisting a yeast-derived PAP1 gene, a yeast-derived NAB6 gene, a yeast-derived CCC1 gene and a yeast-derived MOS2 gene that are capable of activating the DIT1 terminator. Such activation genes and method of applying them to yeasts are described in paragraphs 0040 to 0063 and paragraphs 0074 to 0103 of Japanese Patent Application Publication No. 2015-136303.

The ordinary necessary operations in the methods of preparing the gene expression cassette and vector of the invention, the methods of introducing these into yeasts and the methods of preparing the yeast of the invention are ordinary matters for those skilled in the art, and can be implemented by a person skilled in the art with reference to, for example, the manual of T. Maniatis, J. Sambrook et al. (Molecular Cloning, a Laboratory Manual, Cold Spring Harbor Laboratory, 1982, 1989, 2001) as necessary.

(Method for Producing Substance Using Yeast)

The method disclosed in this description for producing a substance using a yeast may include a step of culturing the yeast of the invention. With this production method, the expression intensity of a desired target gene can be increased by using the yeast terminator of the invention. Because of expression of the target gene is regulated (enhanced) by the yeast terminator of the invention in addition to being controlled by the promoter, which already regulates expression of the target gene, expression of the target gene can be enhanced to a greater degree or controlled in a larger sense.

Examples of the target gene include endogenous genes and/or exogenous genes associated with production of useful substances in general. An exogenous gene may be gene that occurs naturally in organisms other than yeasts, or an artificial gene obtained by modifying a natural gene of a yeast or other organism, or a still more artificial gene.

Moreover, the target gene may be a gene directly associated with production of a substance, or a gene that improves or contributes to the availability of a hemicellulose other than glucose, such as xylose, as a source of energy. An enzyme that breaks down cellulose or hemicellulose into monosaccharides that can be used by yeasts can also be expressed. Typical examples of such enzymes include cellobiohydrolase, endoglucanase and beta-glucosidase, and depending on the type of hemicellulose, other examples include xylanase and beta-xylosidase for breaking down xylan, alpha-arabinofuranosidase and acetylxylan esterase for breaking down xylan side chains, mannanase for breaking down mannan, alpha-galactosidase for cleaving galactose side chains, pectriase and pectinase for cleaving pectin, xyloglucanase for breaking down xyloglucan, and ferulic acid esterase for cleaving the bonds between xylan and lignin.

The produced substance is not particularly limited, and may be a compound that can be produced by yeasts under ordinary conditions for example. Moreover, for example one or two or more enzymes may be substituted or added by genetic recombination in the metabolic system of a yeast to yield a compound that is not an intrinsic metabolite of the yeast. Specific examples include ethanol and other lower alcohols, and lactic acid, acetic acid and other organic acids, as well as 1,3-propanediol, propanol, butanol, succinic acid, ethylene and glycerol, the terpenoids farnesol, geranylgeraniol and squalene (obtained by adding an isoprenoid synthesis pathway), fine chemicals (coenzyme Q10, vitamins and raw materials of these), glycerin (obtained by modifying the glycolytic system), raw materials for plastics and chemical products, and other materials for biorefinery use.

In the step of culturing the yeast of the invention, the yeast may be cultured under appropriate culture conditions according to the type of yeast, the type of target gene, and the type of substance to be produced. That is, the yeast can be cultured by static culture, shaking culture or the like using a medium containing a suitable carbon source such as sucrose together with amino acids, inorganic substances and the like for example. For the aeration conditions, anaerobic conditions, microaerobic conditions aerobic conditions or the like may be selected as appropriate. The culture temperature is not particularly limited, but may be in the range of about 20° C. to 40° C. for example. The culture time is also set as necessary, and may be a few hours to 150 hours for example. The pH may be regulated using an inorganic or organic acid or an alkali solution or the like for example. An antibiotic such as ampicillin or tetracycline may be added to the medium as necessary during culture.

By performing such a culture step, it is possible to produce a substance according to the substance-producing ability of the yeast of the invention. The culture step may be followed by a step of collecting a fraction containing a useful substance from the culture liquid, and a further step of purifying or concentrating this fraction. The collection step, purification step and the like may be selected appropriately according to the substance to be produced and the like.

EXAMPLES

The disclosures of this description are explained in detail below using examples, but these examples do not limit the disclosures of this description.

Example 1

(Search for Mutant DIT1 Terminators that Increase Protein-Producing Activity)

The following procedures were used to search for and identify mutant DIT1t terminators having high activity in comparison with wild type DIT1t.

1. Beginning with the T 30 nucleotides downstream from the nucleotide immediately after the stop codon of the DIT1 gene, 3 nucleotides at a time were sequentially deleted to synthesize 16 kinds of mutant DIT1 terminator DNA fragments having 3-nucleotide deletions. The sequence ID numbers of the nucleotide sequences of the wild-type terminator (d0) and 15 kinds of different mutant terminators (d7 to d21) are given in the table below.

TABLE 1

| Symbol | SEQ. ID. |
|---|---|
| d0 | 1 |
| d2 | 7 |
| d7 | 8 |
| d8 | 9 |
| d9 | 10 |
| d10 | 11 |
| d11 | 12 |
| d12 | 13 |
| d13 | 14 |
| d14 | 15 |
| d15 | 16 |
| d16 | 17 |
| d17 | 18 |
| d18 | 19 |
| d19 | 20 |
| d20 | 21 |
| d21 | 22 |
| m1 | 23 |
| m2 | 24 |
| m3 | 25 |
| m4 | 26 |
| m5 | 27 |
| m6 | 28 |
| m7 | 29 |
| m8 | 30 |
| m9 | 31 |
| m10 | 32 |
| m11 | 33 |
| m12 | 34 |
| m13 | 35 |
| m14 | 36 |
| m15 | 37 |
| m16 | 38 |
| m17 | 39 |
| m18 | 40 |
| m19 | 41 |
| m20 | 42 |
| m21 | 43 |
| m22 | 44 |
| m23 | 45 |
| m24 | 46 |
| m25 | 47 |
| m26 | 48 |
| m27 | 49 |
| m28 | 50 |
| m29 | 51 |
| m30 | 52 |
| d22 | 53 |
| d23 | 54 |

Next, 30 kinds of mutant DIT1 terminator DNA fragments were synthesized by saturation mutagenesis of the AGTTAGTTCG part beginning with the A 50 nucleotides downstream from the nucleotide after the stop codon of the DIT1 gene (for example, C, G and T were each substituted for each A in the wild-type sequence). The sequence ID numbers of the nucleotide sequences of all of the 30 kinds of different mutant terminators (m1 to m30) are also shown in Table 1.

Two other mutant DIT1 terminator DNA fragments were synthesized, a mutant terminator d22 having the deletions of both d7 and d21 and a mutant terminator d23 having the mutation of m22 and the deletion of d22. The sequence ID numbers of the nucleotide sequences of these mutant terminators (d22, d23) are also shown in Table 1.

A 5'-end Kpn1 site and a 3'-end BamHI site for cloning purposes were also synthesized in all of these DNA fragments.

2. Next, a construct was constructed for comparing the activities of the mutant DIT1 terminators. FIG. 1 shows an outline of the construct. To begin with, as shown in FIG. 1, the construct included, between the ClaI and XhoI sites of a pSP73 vector (Promega K.K), a PDC6 upstream region (−822 to −177 from the start codon of the GFP coding region), a TDH3 promoter (−796 to −1 from the start codon), a codon optimized GFP (see Yamanishi, M., Matsuyama, T. (2012) A modified Cre-lox genetic switch to dynamically control metabolic flow in transgenic *Saccharomyces cerevisiae*. ACS Synth. Biol. 1, 172-180), each mutant DIT1 terminator (DIT1t), a TRP1 auxotrophic marker gene, a PDC6 downstream region (+4 to +599 from stop codon), and an ApaI site. Constructs of this configuration are also described in the following references: Yamanishi M, Ito Y, Kintaka R, Imamura C, Katahira S, Ikeuchi A, Moriya H, Matsuyama T. A genome-wide activity assessment of terminator regions in *Saccharomyces cerevisiae* provides a "terminatome" toolbox. ACS Synth Biol, 2, 337-347, Ito Y, Yamanishi M, Ikeuchi A, Imamura C, Tokuhiro K, Kitagawa T, Matsuyama T. Characterization of five terminator regions that increase the protein yield of a transgene in *Saccharomyces cerevisiae*. J Biotechnol, 168, 486-492, Yamanishi, M., Katahira, S., Matsuyama, T. (2011) TPS1 terminator increases mRNA and protein yield in a *Saccharomyces cerevisiae* expression system. Biosci. Biotechnol. Biochem. 75, 2234-2236.

3. Each mutant DIT1 terminator construct was inserted into the genome of the wild-type yeast W303-1a at the PDC6 gene locus as follows. The strains were named according to the type of introduced mutant DIT1 terminator.

3-1. The host wild-type yeast was cultured up to the logarithmic growth stage ($OD_{600}$=0.4 to 0.6) at 30° C. in YPD liquid medium, and treated with a Frozen-EZ Yeast Transformation II kit (Zymo Research) to prepare competent cells.

3-2. The construct was fragmented by reacting it for 3 hours or more at 37° C. with the restriction enzymes ClaI and ApaI.

3-3. 50 µg of each fragmented construct was added to 50 uL of competent cells, and diluted with PEG buffer. This was heated for 45 minutes to transform the cells.

3-4. The transformed yeast cells were washed, suspended in sterile water, and coated on tryptophan selection medium. The medium components were 2% agar, 2% glucose, 0.67% Yeast Nitrogen Base without amino acids (YNB) (Difco, Detroit, Mich.), 0.082% Complete Supplement Mixture (CSM)-TRP (ForMedium, Norfolk, UK) and adenine (40 mg/L). This was static cultured for a day and a night at 30° C., to obtain a transformant colony.

3-5. The resulting colony was cultured in the various selection media, a strain that retained stable growth ability was selected, and introduction of the target gene was confirmed by colony PCR.

4. A NAB6-PAP1 assay was performed to evaluate the activity of the mutant DIT1 terminator strain. NAB6 and PAP1 have previously been identified as DIT1 terminator activation factors, and it is known that these two genes activate the DIT1 terminator by the same pathway (Japanese Patent Application Publication No. 2014-39533). As the activation mechanism, it is thought that NAB6 or another factor binds to the cis-sequence AGUUCG contained in the 3'-UTR of DIT1 to form some kind of complex, and increases production of a protein produced by a gene coding region upstream from the 3'-UTR of DIT1. Consequently, by causing overexpression of NAB6 and PAP1 and evaluating the mutant DIT1 terminators, it is possible to efficiently obtain a mutant DIT1 terminator that can be activated by NAB6 and PAP1. We therefore prepared recombinants overexpressing the NAB6 and PAP1 genes in the mutant DIT1t strain, and performed a NAB6-PAP1 assay comparing changes in the expression enhancing activity of the DIT1t with the activity of the wild type, using GFP fluorescence as a marker. The NAB6-PAP1 assay was performed as described in paragraphs 0074 to 0103 of Japanese Patent Application Publication No. 2014-39533.

4-1. NAB6 (+3952 from start codon −391) and PAP1 (+2149 from start codon −509) were each inserted between the BamHI and XhoI sites of a multicopy pGP564 vector having a LEU2 auxotrophic marker (Thermo Fisher Scientific Inc.) to prepare plasmids pGP564-NAB6 and pGP564-PAP1, and PAP1 (+2149 from start codon −509) was also inserted between the SpeI sites of pGP564-NAB6 to prepare a plasmid pGP564-NAB6-PAP1.

4-2. The host DIT1t strain was cultured up to the logarithmic growth stage ($OD_{660}$=0.4 to 0.6) at 30° C. in YPD liquid medium, and treated with a Frozen-EZ Yeast Transformation II kit (Zymo Research) to prepare competent cells.

4-3. 100 ng of each of the four kinds of plasmids (control strain: pGP564, NAB6 strain: pGP564-NAB6, PAP1 strain: pGP564-PAP1, NAB6+PAP1 strain: pGP564-NAB6-PAP1) was added to 50 uL of mutant DIT1t competent cells, and diluted with PEG buffer. These were heated for 45 minutes to transform the cells. In the case of the 3-nucleotide deletion mutant DIT1t strains d7 to d21, three kinds of plasmids (control strain: pGP564, NAB6 strain: pGP564-NAB6, PAP1 strain: pGP564-PAP1) were introduced, while in the case of the single-nucleotide deletion mutant DIT1t strains m1 to m30 and the composite mutant DIT1t strains d22 and d23, all four kinds of plasmids were introduced.

4-4. These transformed yeasts were washed, suspended in sterile water, and coated on leucine selection medium. The selection medium was composed of 2% agar, 2% glucose, 0.67% Yeast Nitrogen Base without amino acids (YNB) (Difco, Detroit, Mich.), 0.082% Complete Supplement Mixture (CSM)-LEU (ForMedium, Norfolk, UK) and adenine (40 mg/L). These were static cultured for a day and a night at 30° C. to obtain transformant colonies.

4-5. 500 µl of leucine selection liquid medium (the medium components above minus the 2% agar) was poured into each well of a deep 96-well V-bottom plate (Corning Incorporated, 3960), and inoculated with the mutant DIT1t control strains, mutant DIT1t NAB6 strains, mutant DIT1t PAP1 strains and mutant DIT1t NAB6+PAP1 strains, four samples per strain. Each deep well plate was also inoculated with the wild-type DIT1t control strains, NAB6 strains, PAP1 strains and NAB6+PAP1 strains as a standard, four samples per strain.

4-6. The plate was covered with an air-permeable seal (Bio-Bik, BF-400), and cultured overnight at 30° C., 180 rpm in an incubator shaker (Taitec Corporation, MBR-022UP) to prepare a pre-culture.

4-7. 500 µl of leucine selection liquid medium was poured into each well of a new deep 96-well plate and inoculated with 10 µl of the previous culture liquid, and the plate was covered with an air-permeable seal and cultured for 6 hours under similar conditions.

Figure 3:
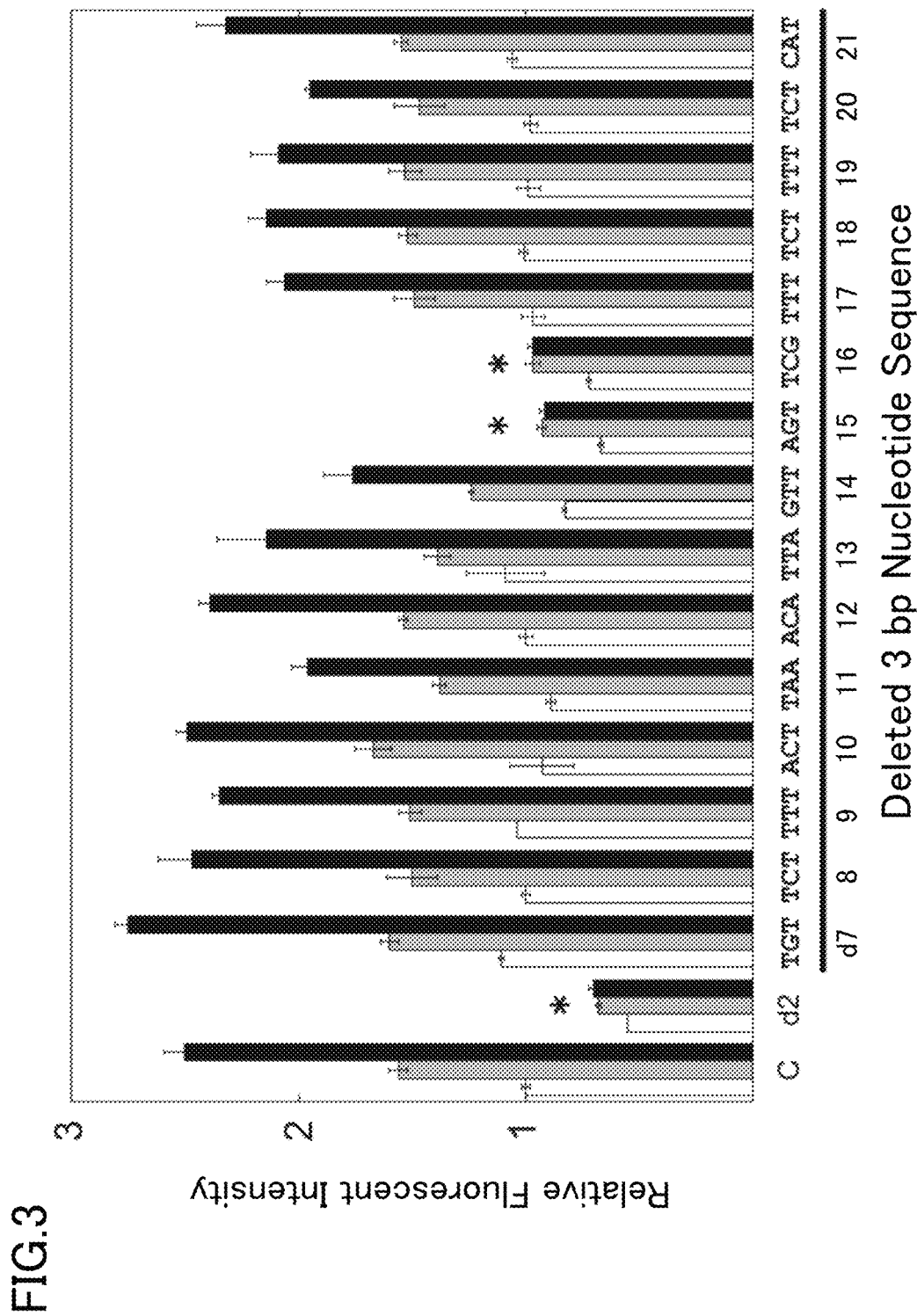
FIG. 3 shows the results of an activity evaluation of 15 kinds of 3-bp deletion mutant DIT1t. The vertical axis shows GFP relative fluorescent intensity in comparison with that of a wild-type DIT1t control strain, and C on the line below the chart indicates the wild type, d2 indicates the 10 bp-deletion mutant d2, the white bars represent control strains, the gray bars represent NAB6 overexpressing strains, the black bars represent PAP1 overexpressing strains, and the errors are standard deviations. The results are average values of 3 to 4 tests.
Figure 4:
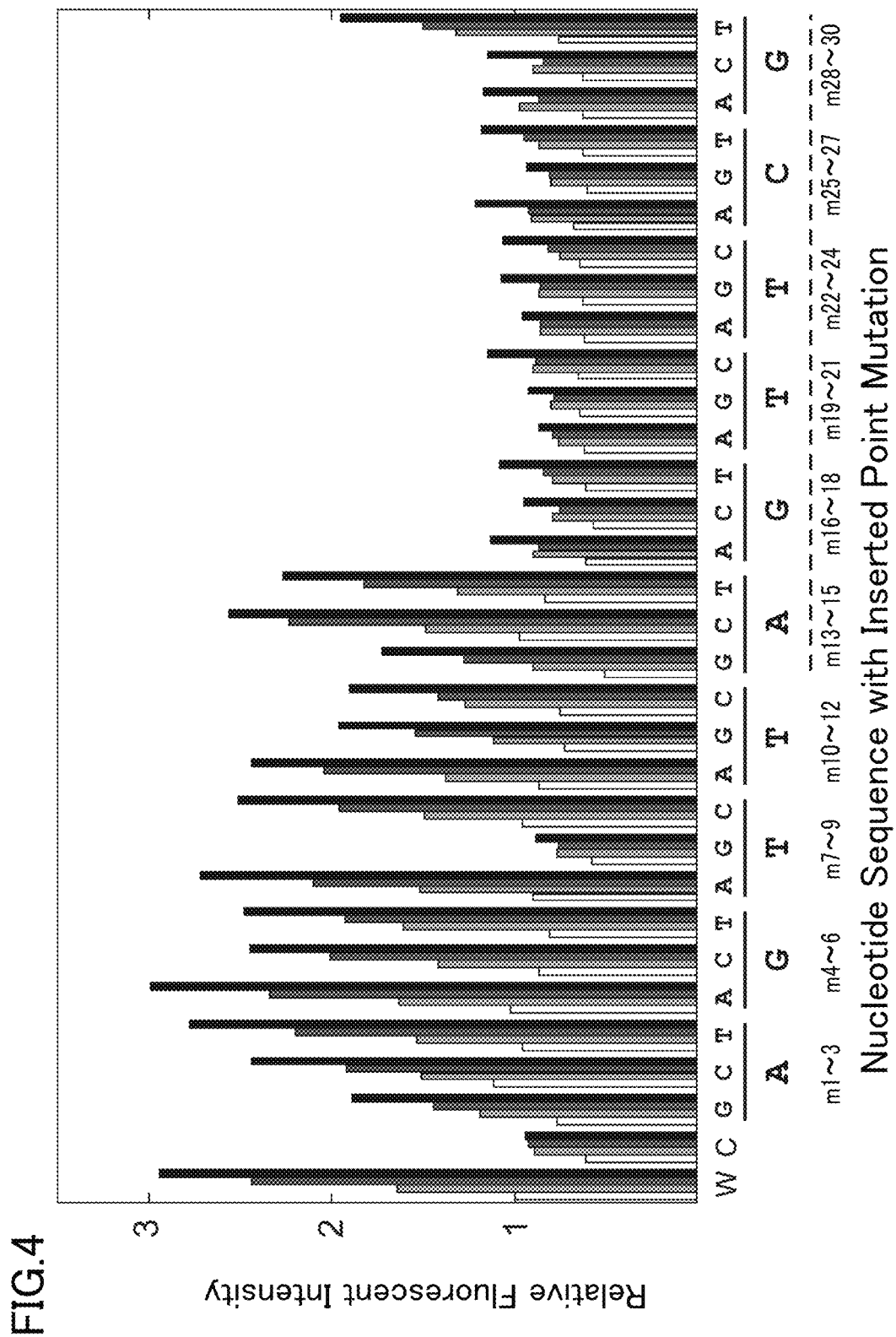
FIG. 4 shows the results of a NAB6+PAP1 assay of the 30 kinds of mutant DIT1t strains m1 to m30 having single-nucleotide mutations. The vertical axis shows relative fluorescent intensity in comparison with the GFP fluorescent intensity of the DIT1t control strain, while on the horizontal axis, W on the first line below the chart indicates the wild type and C indicates the 3 bp-deletion mutant d15, the letters on the second line represent the 10-bp nucleotide sequence into which the point mutations were introduced, and the line above shows the mutated nucleotides in each. The terminator region "AGTTCG" coding for the cis-sequence is indicated with a broken line. The white bars in the chart represent control strains, the light gray bars represent NAB6 overexpressing strains, the dark gray bars represent PAP1 overexpressing strains, and the black bars represent strains simultaneously overexpressing NAB6 and PAP1. The results are all average values of 3 to 4 tests. No errors are shown.
Figure 5:
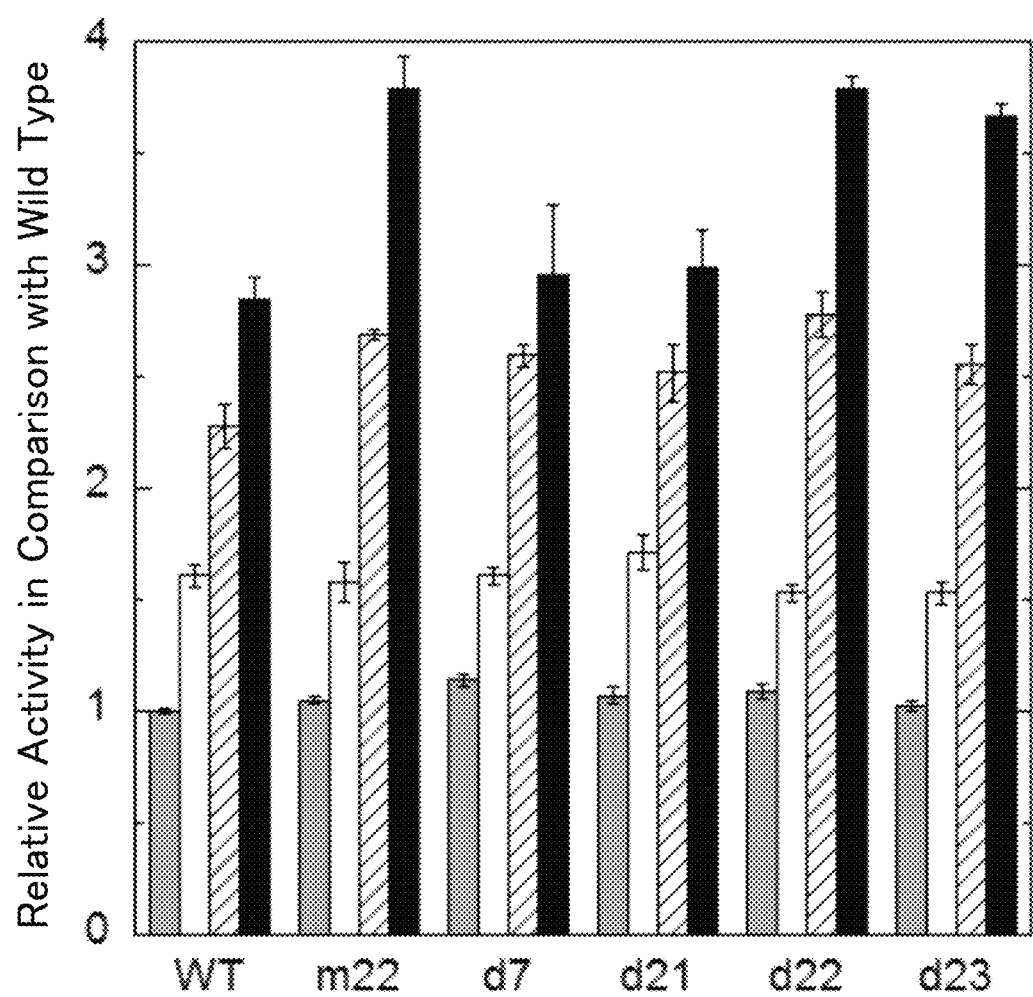
FIG. 5 shows the gene expression enhancing activity of those mutant DIT1t strains that exhibited greater activity than the wild type in the NAB6+PAP1 assay. The vertical axis shows relative fluorescent intensity in comparison with the GFP fluorescent intensity of the wild-type DIT1t control, while on the horizontal axis, the mutant DIT1t strains are shown by gray (control pGP564), white (pGP564-NAB6), crosshatched (pGP564-PAP1) and black (pGP564-PAP1-NAB6) bars. The results are all average values of 4 tests, and the errors are standard deviations.

4-8. The fluorescence of the GFP protein in the yeast cells was excited with a 488 nm laser using a flow cytometer (FCM, Beckman Coulter, Inc., Cell Lab Quanta SC) with a 510/10 filter set, and the fluorescent intensity was measured. The data were analyzed with Igor Pro (WaveMetrix Ltd). FIG. 3 shows the results for the 3-nucleotide deletion mutant DIT1t strains, while FIG. 4 shows the results for mutant DIT1t strains obtained by saturation mutagenesis, and FIG. 5 shows the results for mutant DIT1t strains obtained by effective 3-nucleotide deletion mutation, saturation mutagenesis, and two kinds of composite mutations.

4-9. As shown in FIG. 3, the d7 strain and d21 strain had somewhat higher activity than the wild type. As shown in FIG. 4, moreover, the m22 strain had somewhat higher activity out of the single-nucleotide mutant DIT1t strains. As shown in FIG. 5, moreover, the d7 strain, d21 strain, m22 strain, d22 strain and d23 strain were considered to be mutant DIT1t candidates having higher activity than wild-type DIT1t.

Example 2

Figure 6:
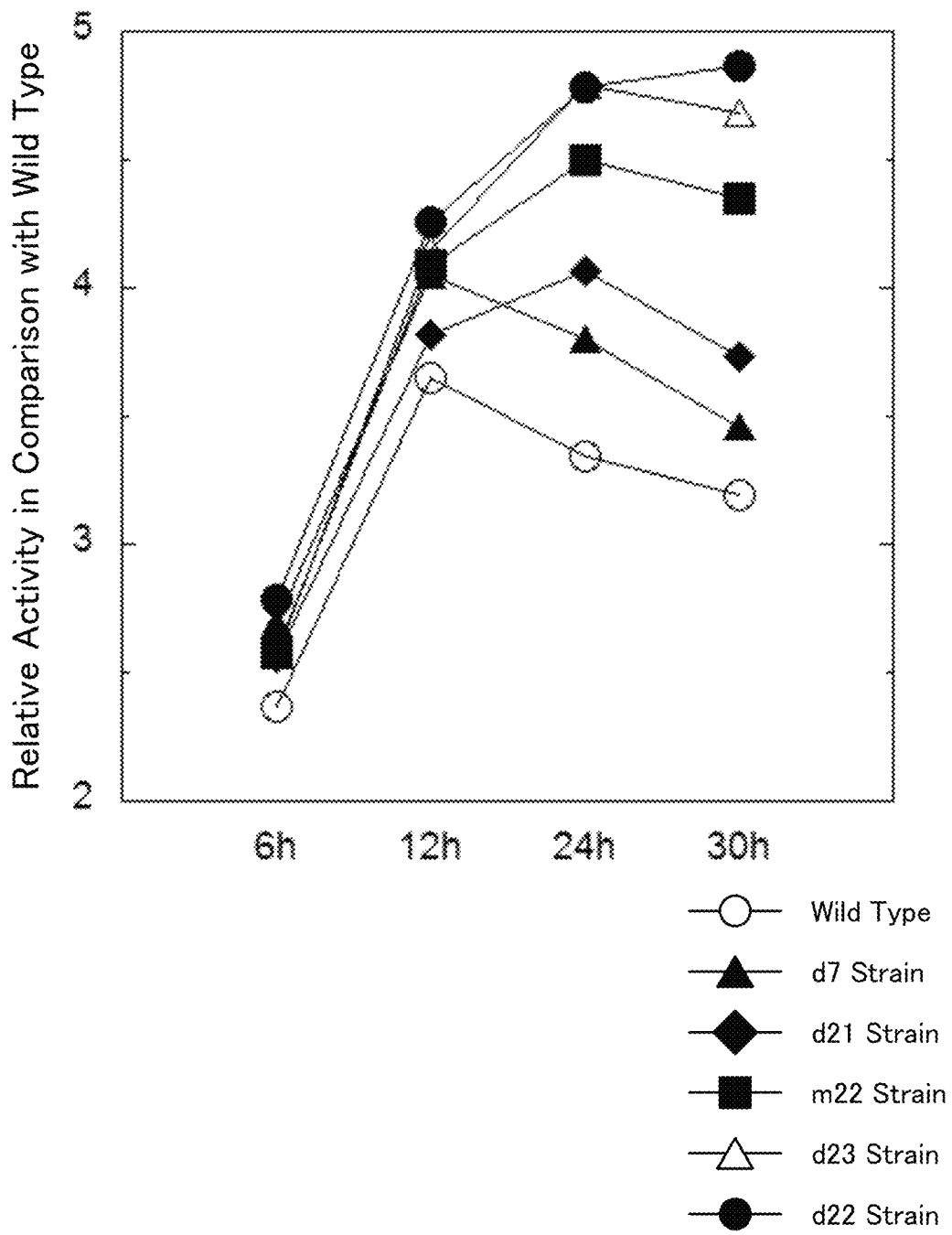
FIG. 6 shows the results of a comparison of the activities of the wild-type DIT1 terminator and mutant DIT1 terminators. Values for relative activity given 1 as the activity of the PGK1 terminator are shown on the vertical axis, while the horizontal axis represents time after transplantation at $OD_{600}=1$ for the wild type (○) and the mutants d7 (▲), d21 (◆), m22 (■), d23 (Δ) and d22 (●). The values are averages from 4 independent tests.

In this example, the activity of mutant DIT1t was evaluated. That is, changes in activity (GFP fluorescent intensity) from the logarithmic growth phase through the stationary phase for the mutant DIT1t candidates selected in Example 1 were investigated over time as in Example 1. Culture from the logarithmic growth phase through the stationary phase was performed by ordinary methods. The PGK1t strain was used in addition to the wild-type DIT1t strain as a control. The results are shown in FIG. 6. In FIG. 6, the activities of the mutant strains are shown as relative values given 1 as the activity of the PGK1t strain.

As shown in FIG. 6, all the candidate mutant DIT1t strains exhibited high activity in comparison with the wild type at each point in time. In particular, the d22 strain and d23 strain exhibited up to 4 times or more the activity of the commonly used PGK1 terminator and CYC1 terminator in the stationary phase, and up to 1.5 times the activity of the wild-type DIT1 terminator, which has the maximum activity obtained with existing technology. Unlike the d22 strain, the d23 strain exhibited a slight drop in activity in the stationary phase. The d22 strain exhibited the strongest activity at all stages.

Example 3

In this example, the construct prepared in Example 1 for the mutant DIT1t-d22 strain was introduced into a parent strain not used in Example 1 or 2, and the effects due to the differences in the parent strain were confirmed. Using the haploid yeast YPH499 as the parent strain, genetic recombination was performed as in Example 1 to prepare a wild-type DIT1t strain and a mutant DIT1t-d22 strain of YPH499, and terminator activity was evaluated as in Example 1. The results are shown in FIG. 7.

Figure 7:
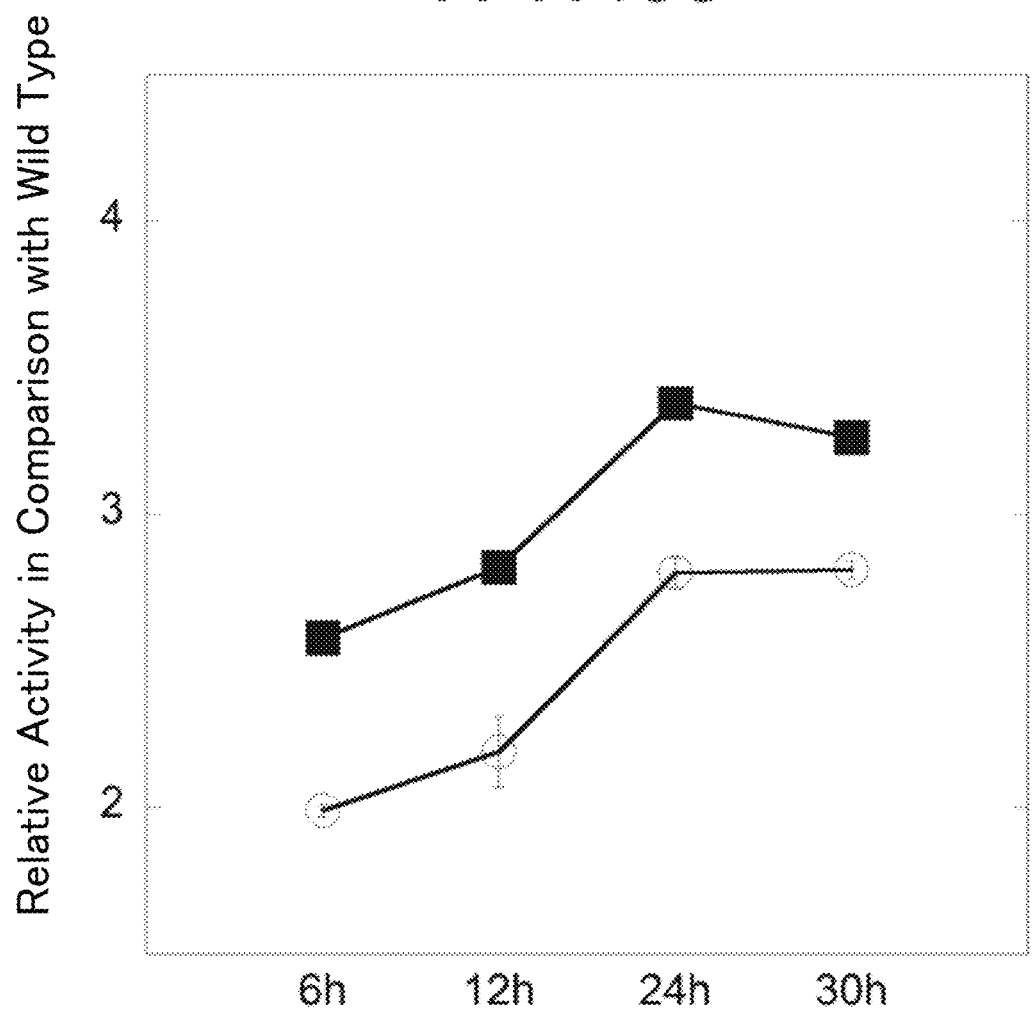
FIG. 7 shows the results of a comparison of the activities of the wild-type DIT1 terminator and a mutant DIT1 (d22) terminator. Values for relative activity given 1 as the activity of the PGK1 terminator are shown on the vertical axis, while the horizontal axis represents time after transplantation at $OD_{600}=1$ for the wild type (○) and the mutant d22 (■). The values are averages from 3 independent tests.

As shown in FIG. 7, in YPH strains, DIT1t-d22 strain (YPH) also exhibited strong terminator activity in comparison with the wild-type DIT1t strain. This shows that mutant DIT1t produces strong terminator activity regardless of the parent strain.

[Sequence Listing Free Text]

SEQ ID NOS:2 to 54: Mutant DIT1 terminators

What is claimed is:

1. A yeast terminator obtained from a yeast DIT1 terminator, wherein
the yeast terminator, when aligned with the nucleotide sequence of SEQ ID NO:1, comprises:
the nucleotide sequence AGTTCG of positions 54 to 59 in the nucleotide sequence of SEQ ID NO:1, and
one or two or more mutations selected from the group consisting of (a) to (c) below:
(a) a first mutation substituting TTTTTCT for the nucleotide sequence TTTTGTTCT of positions 27 to 35 in the nucleotide sequence of SEQ ID NO:1;
(b) a second mutation substituting TCTTTT for the nucleotide sequence TCTCATTTT of positions 69 to 77 in the nucleotide sequence of SEQ ID NO:1; and
(c) a third mutation substituting A for the G of position 51 in the nucleotide sequence of SEQ ID NO:1.

2. The yeast terminator according to claim 1, comprising the first mutation.

3. The yeast terminator according to claim 1, comprising the second mutation.

4. The yeast terminator according to claim 1, comprising the third mutation.

5. The yeast terminator according to claim 1, comprising the first mutation and the second mutation.

6. The yeast terminator according to claim 1, comprising the first mutation, the second mutation and the third mutation.

7. The yeast terminator according to claim 1, comprising a nucleotide sequence of that of positions 1 to 26 in the nucleotide sequence of SEQ ID NO:1.

8. The yeast terminator according to claim 1, comprising a nucleotide sequence of TAAACATTA at positions 42 to 50 in the nucleotide sequence of SEQ ID NO:1.

9. The yeast terminator according to claim 1, comprising a nucleotide sequence of TTTTCTTTT at positions 60 to 68 of the nucleotide sequence of SEQ ID NO:1.

10. The yeast terminator according to claim 1, comprising a nucleotide sequence having 95% or more identity with the nucleotide sequence of positions 78 to 205 of SEQ ID NO:1.

11. A cassette for gene expression in yeasts, the cassette comprising: a promoter region; a cloning site for introducing a coding region of a target gene or the coding region of the target gene; and a terminator region containing the yeast terminator according to claim 1.

12. A vector for gene expression in yeasts, the vector comprising: a promoter region; a cloning site for introducing a coding region of a target gene or the coding region of the target gene; and a terminator region containing the yeast terminator according to claim 1.

13. A recombinant yeast carrying: a promoter region; a coding region of a target gene; and a terminator region containing the yeast terminator according to claim 1.

14. A method for producing a substance using a yeast, comprising providing a sequence for the substance to be produced, culturing the recombinant yeast according to claim 13 and expressing the sequence to produce the substance.

* * * * *